United States Patent
Levitzki et al.

(10) Patent No.: US 9,006,406 B2
(45) Date of Patent: Apr. 14, 2015

(54) EGFR-HOMING DOUBLE-STRANDED RNA VECTOR FOR SYSTEMIC CANCER TREATMENT

(75) Inventors: Alexander Levitzki, Jerusalem (IL); Alexei Shir, Jerusalem (IL)

(73) Assignee: Alexander Levitzki, Jerusalem (IL)

( * ) Notice: Subject to any disclaimer, the term of this patent is extended or adjusted under 35 U.S.C. 154(b) by 823 days.

(21) Appl. No.: 13/141,345

(22) PCT Filed: Dec. 22, 2009

(86) PCT No.: PCT/IL2009/001210
§ 371 (c)(1),
(2), (4) Date: Oct. 11, 2011

(87) PCT Pub. No.: WO2010/073247
PCT Pub. Date: Jul. 1, 2010

(65) Prior Publication Data
US 2012/0021006 A1 Jan. 26, 2012

Related U.S. Application Data

(60) Provisional application No. 61/139,698, filed on Dec. 22, 2008.

(51) Int. Cl.
*C07H 21/02* (2006.01)
*C12N 15/00* (2006.01)
*C12N 15/88* (2006.01)
*A61K 45/00* (2006.01)
*C12N 15/117* (2010.01)

(52) U.S. Cl.
CPC .......... *C12N 15/117* (2013.01); *C12N 2310/17* (2013.01)

(58) Field of Classification Search
None
See application file for complete search history.

(56) References Cited

U.S. PATENT DOCUMENTS

2006/0110746 A1* 5/2006 Andre et al. .................. 435/6

FOREIGN PATENT DOCUMENTS

WO 2004045491 A2 6/2004

OTHER PUBLICATIONS

Ogris et al., Tumor-targeted gene therapy: strategies for the preparation of ligand-polyethylene glycol-polyethylenimine /DNA complexes; J Controlled Release, vol. 91, pp. 173-181, 2003.*
Wolshek et al., Specific Systemic Nonviral Gene Delivery to Human Hepatocellular Carcinoma Xenografts in SCID Mice; Hepatology, vol. 36, No. 5, pp. 1106-1104, 2002.*
Shir et al. "EGF receptor-targeted synthetic double-stranded RNA eliminates glioblastoma, breast cancer, and adenocarcinoma tumors in mice." PLoS Med. 3(1): e6. (Jan. 2006).
Friedrich et al. "RNA Molecules as Anticancer Agents." Seminars in Cancer Biology 14(4): 223-230. (Aug. 2004).
Ciceri et al. "Antitumor effects of HSV-TK-engineered donor lymphocytes after allogeneic stem-cell transplantation." Blood 109(11): 4698-4707. (Jun. 2007).
Butowski N. et al; "A phase II clinical trial of poly-ICLC with radiation for adult patients with newly diagnosed supratentorial glioblastoma: a North American Brain Tumor Consortium (NABTC01-05)" Journal of neuro-oncology 91, pp. 175-182. (2009).
Fujimura T. et a; "Inhibitory effect of the polyinosinic-polycytidylic acid/cationic liposome on the progression of murine B16F10 melanoma" European journal of immunology, 36, pp. 3371-3380 (2006).
Hynes N. E. et al; "ErbB receptors and signaling pathways in cancer" Current Opinion in Cell Biology, vol. 21, Issue 2, pp. 177-184. (2009).
Li Z. "Identification and characterization of a novel peptide ligand of epidermal growth factor receptor for targeted delivery of therapeutics" The FASEB Journal 19 pp. 1978-1985. (2005).
Steven A. Rosenberg; "Overcoming obstacles to the effective immunotherapy of human cancer" PNAS, 105, 35 pp. 12643-12644 (2008).
Salazar A.M et al; Long-term treatment of malignant gliomas with intramuscularly administered polyinosinic-polycytidylic acid stabilized with polylysine and carboxymethylcellulose: an open pilot study. Neurosurgery 38, pp. 1096-1103. (1996).
Song S. et al; "Peptide ligand-mediated liposome distribution and targeting to EGFR expressing tumor in vivo" International Journal of Pharmaceutics 363 pp. 155-161. (2008).

* cited by examiner

*Primary Examiner* — Jennifer Dunston
*Assistant Examiner* — Addison D Ault
(74) *Attorney, Agent, or Firm* — Fox Rothschild LLP

(57) ABSTRACT

An epidermal growth factor receptor (EGFR)-homing vector comprising a double-stranded RNA (dsRNA) molecule with an EGFR-binding peptide or polypeptide, is disclosed for use in combination with immune cells for treatment of cancer overexpressing EGFR.

2 Claims, 13 Drawing Sheets

→ UT    ▫ pGlu/MPPE+PBMC
▪ PBMC   ■ PolyIC/MPPE
▲ pGlu/MPPE   ● PolyIC/MPPE+PBMC ◆ UT
■ HBG
▲ PolyIC/MPPE

EGFR-HOMING DOUBLE-STRANDED RNA VECTOR FOR SYSTEMIC CANCER TREATMENT

CROSS-REFERENCE TO RELATED APPLICATIONS

The present application is the U.S. National Phase of International Patent Application Serial No. PCT/IL2009/001210, filed Dec. 22, 2009, which claims priority to U.S. Provisional Patent Application Ser. No. 61/139,698, filed Dec. 22, 2008, the disclosures of which are hereby incorporated by reference in their entireties.

FIELD OF THE INVENTION

The present invention is in the field of cancer therapy and relates to vectors comprising double stranded RNA (dsRNA) with an EGFR-binding agent capable of specifically directing the dsRNA to EGFR overexpressing cancer cells thus mobilizing the immune system for treatment of EGFR overexpressing tumors.

Abbreviations: dsRNA: double-stranded RNA; EGF: Epidermal Growth Factor; EGFR: EGF Receptor; PBMC: peripheral blood mononuclear cells; PEG: poly(ethylene glycol); PEI: polyethyleneimine; pIC, PolyIC: polyinosinic-polycytidylic acid double-stranded RNA; pIC/MPPE: PolyIC/Melittin-branched Polyethyleneimine-Polyethyleneglycol-EGF pIC/PPE: PolyIC/linear Polyethyleneimine-Polyethyleneglycol-EGF; pIC/PPGE11: PolyIC/linear Polyethyleneimine-Polyethyleneglycol-(peptide)GE11.

BACKGROUND OF THE INVENTION

Epidermal Growth Factor Receptor (EGFR) is overexpressed in a variety of solid human tumors including non-small-cell-lung-carcinoma, breast cancer, glioblastoma, head and neck squamous cell carcinoma, colorectal cancer, adenocarcinoma, ovary cancer, bladder cancer and prostate cancer (Hynes et al., 2009). The American Cancer Society's annual estimate of new cancer cases and deaths projects 1,437,180 new cancer cases in the United States in 2008 and 565,650 cancer deaths. The cause of most cancer deaths is metastasis of the cancer into internal organs, which is virtually impossible to treat by conventional methods. A significant fraction of all cancer related deaths are associated with overexpression of EGFR. Thus EGFR is one of the most important candidates for targeted cancer therapy.

The two most advanced EGFR-targeted therapies are small membrane permeable EGFR kinase inhibitors and anti-EGFR antibodies, which prevent receptor activation and/or lead to receptor down-regulation. These agents induce temporary or partial remission and convey some survival benefits, but do not actually cure patients. This is most likely because EGFR is not essential for the survival of the targeted cancer cells.

PolyIC, a synthetic polyinosinic-polycytidylic acid double-stranded RNA, is a known cytotoxic agent. Intratumoral or peritumoral administration of non-targeted PolyIC has been demonstrated to be effective in anti-tumor immunotherapy (Fujimura et al., 2006). Such treatment is limited to localized tumors only as has been shown by attempts to systemic application of non-targeted PolyIC to treat cancer. The survival benefit was minimal while pronounced systemic toxicity was observed (Butowski et al., 2009; Salazar et al., 1996). The weak effect was most likely caused by the failure to introduce a sufficient dose of PolyIC into the tumor cells. Most of the non-targeted PolyIC probably scattered through normal tissues entering into non-cancer cells and inducing toxic reactions.

Recently we developed a strategy that utilizes the high level of expression of EGFR, rather than its activity per se, as the Achilles' heel of the tumor. This was achieved by utilizing an EGFR homing chemical vector loaded with PolyIC (Shir et al., 2006; WO 04/045491). The intratumoral application of PolyIC/Melittin-Polyethyleneimine-Polyethyleneglycol-EGF (PolyIC/MPPE) to EGFR overexpressing glioblastoma ($\sim 1\times10^6$ receptors/cell) grown intracranially and to EGFR overexpressing breast and epidermoid carcinomas grown as xenografts in nude mice, led to complete elimination of these localized tumors, curing the mice. Furthermore, tumors comprising a 1:1 mixture of cells overexpressing wild type EGFR and cells harboring the mutant EGFRvIII, which does not internalize the vector, were also completely eradicated. This "bystander effect" was due to the antiproliferative cytokines such as interferon-α, generated at the tumor site by the PolyIC/MPPE affected tumor cells.

SUMMARY OF INVENTION

The present invention relates to an epidermal growth factor receptor (EGFR)-homing vector comprising a double-stranded RNA (dsRNA) molecule with an EGFR-binding peptide or polypeptide, for use along with immune cells in treatment of cancer overexpressing EGFR.

The present invention further relates to a method for treatment of cancer characterized by EGFR overexpressing cells, said method comprising systemically administering to a patient in need a combination of: (i) an EGFR-homing vector comprising a dsRNA molecule with an EGFR-binding peptide or polypeptide capable of targeting the vector to tumor cells overexpressing EGFR; and (ii) immune cells.

In certain embodiments, the present invention provides a pharmaceutical composition for systemic administration comprising a pharmaceutically acceptable carrier and an EGFR-homing vector comprising a double-stranded dsRNA molecule with an EGFR-binding polypeptide.

In other certain embodiments, the invention provides a method for treatment of cancer characterized by EGFR-overexpressing cells said method comprising systemically administering to a patient in need an effective amount of an EGFR-homing vector comprising a double-stranded dsRNA molecule with an EGFR-binding polypeptide.

In certain embodiments, the EGFR-homing vector further comprises a nucleic acid carrier, for example, composed of polyethyleneimine (PEI) covalently linked to polyethylene glycol (PEG), the dsRNA is polyIC non-covalently associated with the PEI moiety of the carrier and the EGFR-binding peptide or polypeptide is EGF or the peptide GE11 covalently linked to the PEG moiety of the carrier.

The vectors, compositions and methods of the invention are intended for treatment of a cancer selected from non-small-cell-lung-carcinoma, breast cancer, glioblastoma, head and neck squamous cell carcinoma, colorectal cancer, adenocarcinoma, ovary cancer, bladder cancer or prostate cancer, and metastases thereof.

BRIEF DESCRIPTION OF DRAWINGS

FIG. 3A. To demonstrate the PBMC-mediated bystander effect, 100,000 MDA-MB-468 cells were seeded into 6-well plates and grown overnight with 2 ml medium (Shir et al., 2006). Cells were then transfected with Poly IC/MPPE, at the indicated concentrations. 48 hrs after transfection 0.5 ml of medium from the transfected cells ("conditioned medium") was added to 500,000 PBMCs which had been seeded 24 hrs earlier into 24-well plates and grown in 0.5 ml medium. 0.1 ml of medium from the challenged PBMCs was then exchanged for 0.1 ml medium from additional non-transfected MDA-MB-468 cells ("indicator cells") seeded 24 hrs earlier. Survival of these cells was determined by methylene blue assay, 48 hours after challenge with the medium from the PBMCs (black bars in graph). In parallel, to show the direct bystander effect, 0.1 ml of conditioned medium was used to replace 0.1 ml medium from non-transfected MDA-MB-468 cells ("indicator cells") seeded 24 hrs earlier into 96 well plates and grown in 0.2 ml medium. Survival of these cells was determined 48 hours after addition of the conditioned medium using methylene blue (hatched bars); FIG. 3B shows the bystander effect of poly IC transfected MDA-MB-468 cells on untransfected U138MG cells; FIGS. 3C-3D show the bystander effect of poly IC transfected A431 cells on untransfected A431 cells and untransfected U138MG cells, respectively. "No treatment" shows survival of indicator cells that did not undergo any medium exchange. "PBMCs UT" shows survival of indicator cells treated with medium from unchallenged PBMCs. "UT" shows survival of indicator cells treated with medium from PBMCs challenged by the medium of untransfected cells. "No PBMCs" (gray bars) indicates survival when conditioned medium was added to PBMC growth medium but in the absence of PBMCs, and this was used 48 hours later to challenge the indicator cells. This latest control was used to detect a possible residual direct bystander effect of the conditioned medium after incubation in PBMCs medium in the absence of PBMCs.

DETAILED DESCRIPTION OF THE INVENTION

Figure 1A:
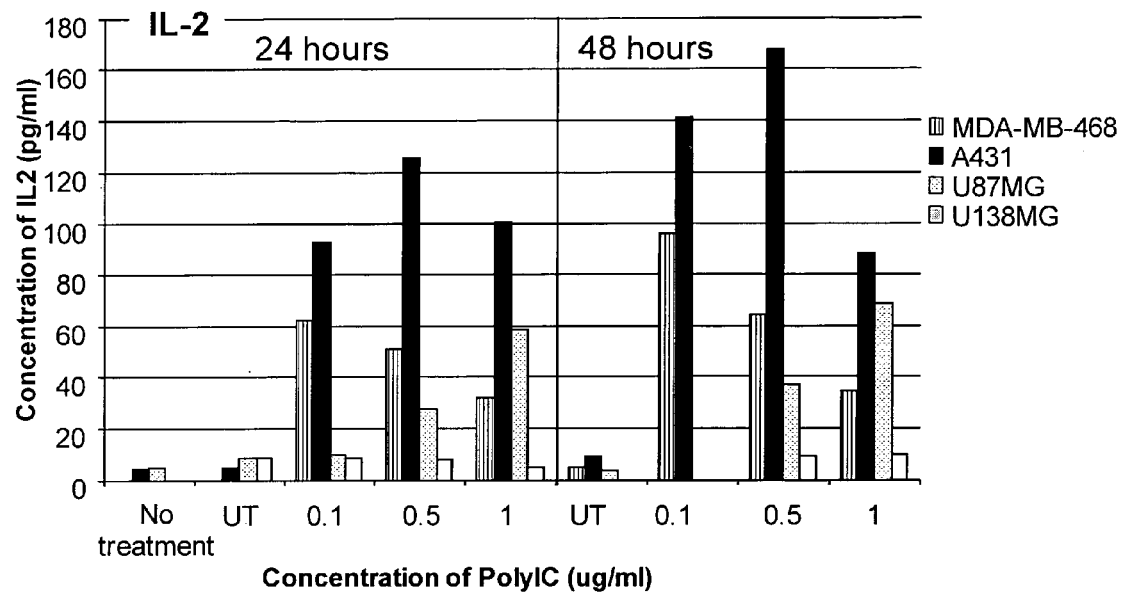
FIGS. 1A-C depict bar graphs showing that PBMCs are selectively activated by the medium of PolyIC/MPPE transfected MDA-MB-468 and A431 cells. 500,000 PBMCs were seeded into 24 well plates and grown overnight in 0.5 ml medium as described in Methods. The PBMCs were then challenged with 0.5 ml of medium removed from A431, MDA-MB-468, U87MG or U138MG cells transfected with PolyIC/PEI-PEG-EGF+PEI-Mel 48 hrs after transfection. The PBMC medium was collected 24 and 48 hours after the challenge and IFN-γ, IL-2 and TNF-α were measured using ELISA assays. (1A) Expression of IL-2 in the medium of PBMCs, 24 and 48 hrs after challenge. (1B) Expression of IFN-γ in the medium of PBMCs, 48 hrs after challenge. (1C) Expression of TNF-α in the medium of PBMCs, 48 hrs after challenge. "No treatment" shows expression of the cytokines in unchallenged PBMCs. "UT" shows expression of the cytokines by PBMCs challenged with the medium of untransfected cells. Poly glutamic acid (pGlu)/MPPE was applied as control.

In certain embodiments, the present invention provides an EGFR-homing vector comprising a dsRNA molecule, an agent known for its cytotoxicity and cell penetration capacity; with an EGFR-binding peptide or polypeptide capable of targeting the vector to tumor cells overexpressing EGFR, for use in combination with immune cells for treatment of EGFR overexpressing tumors.

In certain other embodiments, the present invention provides a method for treatment of cancer characterized by EGFR overexpressing cells, said method comprising systemically administering to a patient in need a combination of: (i) an EGFR-homing vector comprising a dsRNA molecule with an EGFR-binding peptide or polypeptide capable of targeting the vector to tumor cells overexpressing EGFR; and (ii) immune cells.

The dsRNA molecule for use in the present invention is a synthetic double-stranded molecule that may include a different, but preferably the same, number of ribonucleotides in each strand. Each strand of the dsRNA molecule may comprise the same or different types of ribonucleotides including inosinate (I), cytidylate (C), adenylate (A), guanylate (G) and uridylate (U). In certain preferred embodiments, each of the strands is composed of a single type of ribonucleotides and, more preferably, the ribonucleotides of the two strands are matching ribonucleotide pairs, for example, adenylate-uridylate or inosinate-cytidylate pairs.

In certain preferred embodiments, the dsRNA is wholly composed of matching ribonucleotide pairs, more preferably inosinate (I)-cytidylate (C) pairs. Thus, the dsRNA molecule includes a polyinosinic acid strand and a polycytidylic acid strand and is herein referred to as "polyIC" of "pIC". Poly IC may stimulate the release of cytotoxic cytokines and, by inducing interferon-gamma production may increase the number and tumoricidal activities of various immunohematopoietic cells The polyIC of the vector of the invention may be composed of RNA strands each comprising at least 22, preferably at least 85 ribonucleotides. In certain embodiments, each strand has a number of ribonucleotides within the range of 100-300.

The EGFR-binding peptide or polypeptide capable of targeting the vector to tumor cells overexpressing EGFR may be a polypeptide, for example, EGF itself. In certain embodiments, the EGFR-binding peptide is a peptide ligand for EGFR such as the 12-mer peptide GE11 of the sequence YHWYGYTPQNVI (SEQ ID NO: 1) isolated from a phage library, synthesized and shown to bind to EGFR competitively with EGF (Li et al., 2005; Song et al, 2008).

The dsRNA is preferably non-covalently associated to the targeting moiety of the vector. This facilitates the dissociation of the dsRNA from the targeting moiety following arrival to the targeted cell/tissue and its internalization in the tumor cell/tissue causing the production of chemokines that will attract immune cells to the tumor site.

The non-covalent association of the polyIC with the targeting molecule is preferably effected via a nucleic acid carrier which is associated with both the dsRNA molecule and the targeting moiety.

The nucleic acid carrier may comprise a polycationic polymer and/or a non-ionic water-soluble polymer.

Polycationic polymers that can be used as nucleic acid carriers include poly-L-lysine or, preferably, polyethyleneimine (PEI). PEI is a polycationic polymer with the capacity to associate non-covalently with double stranded RNA molecules due to the polyanionic nature of the latter, thereby neutralizing the negative electrostatic charges of the dsRNA molecule, and hence counteracting any tendency of the dsRNA to chemically interact with anionic molecules. The use of polyethyleneimine in transfecting cells with polynucleotides is well known in the art; however, in its traditional use, polyethyleneimine carries the dsRNA to the cell membrane, adheres to it, undergo endosomal uptake and subsequent cytoplasmic delivery of the dsRNA upon endosomal membrane degradation. In contrast, in the present invention, the targeting and binding of the dsRNA to the EGFR receptor on the cancer cell surface is the main avenue for the internalization of the dsRNA.

The non-ionic water-soluble polymer for use as nucleic acid carrier in the present invention is preferably poly(ethylene glycol) (PEG), which is biocompatible, biologically inert and is widely used for carrying drugs in vivo.

In certain preferred embodiments, the dsRNA carrier used in the invention comprises both polyethyleneimine (PEI) and polyethyleneglycol (PEG), which is covalently linked to the PEI. PEG confers excellent water-solubility and tissue distribution to the complex and increases its serum half life.

The PEI may be branched or linear and has a molecular weight selected from about 1-25 kDa, about 5-23 kDa, about 15-25 kDa, and the PEG has a molecular weight selected from about 0.3-50 kDa, about 1-20 kDa, about 3-10 kDa. In certain embodiments, the dsRNA carrier comprises branched PEI of 25 kDa In certain preferred embodiments, the dsRNA carrier is composed of linear PEI of 22 kDa covalently linked to PEG of 3, 4 kDa.

The targeting moiety of the vector, namely, the EGFR-binding peptide or polypeptide is preferably covalently coupled to the PEG moiety of the PEI-PEG conjugate, while the polyIC is non-covalently associated with the PEI moiety, for example, by ionic association.

In certain embodiments, the nucleic acid carrier may further comprise a compound capable of facilitating degradation of an endosomal membrane, thus facilitating release of the dsRNA molecule from a target cell/tissue endosome into the cytoplasm, where the dsRNA optimally mediates cytotoxicity. In certain embodiments, this compound is melittin or a melittin derivative, which is preferably covalently associated with the polyethylene imine of the dsRNA carrier.

Examples of EGFR-homing vectors that can be used according to the invention include, without limitation, the vectors herein designated pIC/MPPE (comprising polyIC/melittin-branched 25 kDa PEI-PEG-mEGF, described in Shir et al., 2006 and WO 04/045491) and the novel vectors pIC/PPE (comprising polyIC/linear 22 kDa PEI-PEG-mEGF) and pIC/PPGE11 (comprising polyIC/linear 22 kDa PEI-PEG-peptide GE11).

Thus, in certain embodiments, the present invention provides the novel EGFR-homing vectors pIC/PPE and pIC/PPGE11, herein characterized as second generation vectors (vis-à-vis the first generation vectors such as pIC/MPPE described in WO 04/045491).

The second generation vectors do not comprise melittin and comprise linear PEI instead of branched PEI. In addition, in one of the second generation vectors, the recombinant mouse EGF (mEGF) was replaced with the 12-mer peptide GE11. Besides simplification of the procedure of preparation of the second generation vectors in comparison with the first generation, the present inventors have also found that substitution of the branched PEI with the linear PEI afforded higher efficiency in killing cancer cells. This is rather surprising since in the second generation vectors there is only one EGF molecule on each linear PEI molecule vs. several EGFs on the branched PEI of the first generation vectors and a lower affinity to EGFR could be expected for the second generation vectors.

For a tumor to become established it must avoid elimination by the immune system. Many cancers develop mechanisms of inhibiting immune surveillance and can even grow in the presence of immune lymphocytes that recognize cancer antigens. The mechanisms of this local inhibition are not clear, although many theories have been examined. PolyIC, a potent adjuvant, and interferon, a strong immune activator, may well overcome this local inhibition and activate preexisting cancer specific immune lymphocytes, in addition to attracting and activating other immune cells.

We have previously shown (Shir et al., 2006) that cancer cells transfected with EGFR-targeted poly IC secrete the cytokines Gro-α (growth regulated oncogene-alpha) and IP-10, which are known to be able to attract immune cells. It was not clear, however, if these cytokines were secreted in sufficient amounts to actually cause the immune cells to accumulate at the site of the cancer cells.

It has been found in accordance with the present invention that these cytokines, induced by targeted PolyIC, do attract immune cells to the transfected tumor and strongly enhance the efficiency with which cancer cells are killed. This induces a significant synergistic effect, leading to the complete elimination of disseminated tumors, even when treated from a distance with a low total dose of EGFR-targeted poly IC (See Example 6). Activated immune cells strongly enhance the bystander effect brought about by IFN-α (See Example 4), which should facilitate the killing of heterogeneous cancers. Since PolyIC/MPPE is targeted selectively to cancer cells, we do not expect significant systemic immunotoxic reactions to occur. The fact that human PBMCs injected into mice did not induce any Graft versus Host reaction, while inducing a strong antitumor reaction, supports this assumption As mentioned hereinabove, intratumoral or peritumoral administration of non-targeted PolyIC has been demonstrated to be effective in anti-tumor immunotherapy (Fujimura et al., 2006). Such treatment is limited to localized tumors only. In contrast, EGFR-targeted PolyIC is efficient in the treatment of disseminated tumors that are impossible to treat by local therapy.

EGFR-targeted PolyIC can thus be combined with several cancer immunotherapies as taught by the present invention. These cancer immunotherapies include cancer vaccines and cancer-targeted (engineered or extracted) T cells. To mediate anti-tumor effects in vivo, cancer-targeted T cells must traffic to the tumor site, extravasate from the circulation, and then mediate effector functions to cause destruction of cancer cells (Rosenberg, 2008). IP-10 and Gro-alpha strongly induced by targeted PolyIC selectively in tumor cells (Tables 2, 3) should facilitate both traffic to tumor and extravasation, while interferon should enhance T cell mediated cancer killing.

In addition, allogeneic immune cell transplantation to activate graft versus tumor reactions (Ciceri et al., 2007) can be combined with the EGFR-homing vectors of the present invention as shown herein. Injection of foreign PBMCs into PolyIC/MPPE treated mice in the present invention (FIGS. 5B, C) actually resembles such a combination. Grafted immune cells should confer a stronger antitumor effect than the patient's own immune cells.

Examples of immune cells for use in combination with the EGFR-homing vector of the present invention are tumor-infiltrating T-cells (TILs), tumor-specific engineered T-cells, or peripheral blood mononuclear cells (PBMCs). The engineered T-cells are cells that have been genetically reprogrammed or "redirected" to express tumor-reactive T-cell receptor (TCR) or chimeric TCR molecules displaying antibody-like tumor recognition capacity known as "T-bodies". The T-body approach combines antibody recognition and T cells effector function. It is based on T cells expressing chimeric receptors composed of antibody-derived Fv or scFv as their extracellular recognition elements joined to lymphocyte triggering molecules. Unlike antibodies, T cells are well suited to penetrate and destroy solid tumors.

The immune cells may be administered concomitantly with the vector, but preferably the vector and the immune cells are administered sequentially. In certain preferred embodiments, the vector is administered systemically first, followed by the administration of the immune cells at a desired interval. Importantly, the vector and the immune cells exhibit synergy in killing the cells of a tumor.

In view of the experimental results obtained in mice with the vector of the present invention in combination with PBMC, this combined therapy may be beneficial and lead to a complete cure in cancer patients with a functional immune system.

Thus, here we demonstrate, for the first time, a strategy to eradicate disseminated EGFR overexpressing tumors in SCID mice, whose immune system has been reconstituted with human peripheral blood lymphocytes (PBMC). Intravenous delivery of mellitin-polyethyleneimine-pololyethyleneglycol-EGF (PolyIC/MPPE) for 4 days, followed by on the $5^{th}$ day by one intraperitoneal injection of 4 million PMBC, induced the complete cure of SCID-NOD mice with pre-established disseminated EGFR overexpressing tumors, with no adverse side effect. The immune cells and the cytokines they produce are localized to the tumor site of the treated animal. Twelve months after treatment cessation, the treated mice remain cancer-free and healthy. We further demonstrate here that the immune system homes to the site of the tumors, due to the chemokines produced by the internalized polyIC, indicating that an EGFR-homing vector loaded with polyIC can mobilize the immune system to treat and possibly cure patients with disseminated EGFR overexpressing tumors.

The combination EGFR-homing vector/immune cells of the present invention can be used in treatment of cancer characterized by expression of EGFR. The term "expression" as used herein should be understood to include also the term "overexpression", which by its nature is a relative term often assessed in the art by measuring relative gene amplification or the number of receptors present on a cancer cell as compared with the number of receptors present on a normal cell, for example as shown in Table 1. Thus, overexpression may be defined as two-fold or greater amplification of the EGFR gene, as determined by fluorescent in-situ hybridization (FISH), or as a positive (1+, 2+, or 3+) staining using anti-EGFR antibodies in an immunohistochemistry (IHC) assay. Other criteria used in the art to determine overexpression is the fraction of cell membrane labeled with a specific antibody; thus overexpression of EGFR may be defined as at least 1% membranous staining and 1+ intensity, or at least 10% membranous staining. Furthermore, cells may be classified as cells that do not express, or have undetectable levels of EGFR, cells expressing low levels of EGFR (about 1000 to about 100,00 receptors/cell), medium levels of EGFR (about 10,000 to about 100,000 receptors/cell) and cells expressing high levels of EGFR (about $1 \times 10^6$ or more receptors/cell).

Therefore, the cancer susceptible to treatment using the combinations of the present invention are cancers characterized by two-fold or greater amplification of the EGFR gene, positive (1+, 2+, or 3+) IHC assay, at least 1%, or at least 10% membranous staining, medium levels of EGFR and preferably cancer cells characterized by high levels of EGFR.

The term "treating cancer" as used herein refers to the inhibition of the growth of cancer cells. Preferably such treatment also leads to the regression of tumor growth, i.e. to the decrease in size or complete regression of the tumor. In preferred embodiments, the term refers to treatment and alleviation or complete cure of disseminated tumors, namely, of metastases.

The terms "tumor" and "cancer" are herein used interchangeably. In particular, the combination of the present invention is useful in the treatment of a cancer overexpressing EGFR selected from non-small-cell-lung-carcinoma, breast cancer, glioblastoma, head and neck squamous cell carcinoma, colorectal cancer, adenocarcinoma, ovary cancer, bladder cancer and prostate cancer, and metastases thereof.

TABLE 1

Prevalence of HER1/EGFR overexpression/amplification in various clinical studies.

| Source | N | Definition of HER1/EGFR overexpression or EGFR amplification | Percentage of tumors with HER1/EGFR overexpression or EGFR amplification |
|---|---|---|---|
| Dancer et al, 2007, Oncol. Rep., 18: 151-55 | 32 | Two-fold or greater amplification of the EGFR gene by FISH | 65% |
| Bloomston et al, 2006, Dig. Surg. 23: 74-9 | 71 | 1+ or higher staining by IHC | 69% |
| Thybusch-Bernhardt et al, 2001, J Surg Investig 2: 393-400 | 24 | Positive staining by IHC | 33% |
| Onn et al, 2004, Clin Cancer Res 10: 136-143 | 111 | 2 or 3 staining by IHC | 60% |
| Rusch et al, 1993, Cancer Res 53: 2379-85 | 44 | Increased detection by Northern analysis | 45% |
| Selvaggi et al, 2004, Ann Oncol 15: 28-32 | 48 | 2+ or 3+ staining by IHC | 37% |
| Ohtsuka et al, 2006, 1: 787-795 | 48 | 2+ or 3+ staining by Western blotting | 40% |

In our previous disclosure with the first generation vectors (Shir et al., 2006), we have shown successful eradication of localized tumors by intratumoral injection of polyIC-EGFR targeted vectors. This did not teach us that it would be possible to treat disseminated tumors by systemic administration of the vectors, because it was not at all clear if a therapeutically effective amount of vector would reach the tumors.

We have now found and show here for the first time in the Examples below that systemic administration of EGFR-targeted PolyIC is effective in eradicating tumors even at surprisingly low concentrations (as low as 10 ng/ml pIC), that one skilled in the art would not have expected to be high enough to accumulate in the tumor in therapeutically effective levels. In addition, another advantage is that EGFR-targeted PolyIC affects cancer cells only, leaving normal cells unharmed.

As disclosed previously by us, EGFR-targeted PolyIC vector exerts a strong bystander effect, that is, it kills EGFR overexpressing cells as well as neighboring tumor cells, whether or not they express EGFR or its mutated version EGFRvIII. It was shown that the EGFR overexpressing cells transfected with EGFR-targeted PolyIC secret the anti-proliferative cytokine IFN-α that probably caused at least part of the bystander effect. This is crucial, because even tumors showing strong overexpression of EGFR are commonly heterogeneous with respect to EGFR expression. At the same time, EGFR-targeted PolyIC is highly selective for tumor cells, with minimal toxic effects on the surrounding normal tissues as well as on distant normal tissues. The targeted PolyIC quickly activates multiple antiproliferative/pro-apoptotic pathways, minimizing the likelihood of mutations leading to drug resistance.

Thus, in certain embodiments, the EGFR-homing vectors disclosed herein (both the first and second generation vectors) are intended for systemic administration.

The present invention thus further provides a pharmaceutical composition for systemic administration comprising a pharmaceutically acceptable carrier and an EGFR-homing vector comprising a double-stranded dsRNA molecule with an EGFR-binding polypeptide.

The present invention still further provides a method for treatment of cancer characterized by EGFR-overexpressing cells, said method comprising administering systemically to a patient in need an effective amount of an EGFR-homing vector comprising a double-stranded dsRNA molecule with an EGFR-binding polypeptide.

In certain embodiments, the present invention relates to a method for treatment of cancer characterized by overexpression of EGFR via mobilization of the immune system, which comprises systemically administering to a subject in need a therapeutically effective amount of an EGFR-homing vector comprising a double-stranded dsRNA molecule with an EGFR-binding polypeptide, thus generating cytokines that attract immune cells to the tumor sites and causing enhancement of the efficiency of tumor cell killing The pharmaceutical compositions for use in accordance with the present invention may be formulated in conventional manner using one or more pharmaceutically acceptable carriers comprising excipients and auxiliaries. Techniques for formulation and administration of drugs may be found, for example, in "Remington's Pharmaceutical Sciences", Mack Publishing Co., Easton, Pa., latest edition.

The pharmaceutical compositions of the present invention are formulated for systemic administration by any suitable route, for example, for parenteral delivery including intramuscular, intravenous, subcutaneous, intrathecal, or intraperitoneal injection.

For any composition for used in the method of the invention, the therapeutically effective amount or dose can be estimated initially from in-vitro and cell culture assays. For example, a dose can be formulated in animal models to achieve a desired concentration or titer. Such information can be used to more accurately determine useful doses in humans. As shown below in the Examples, a dose of 5 µg vector/mice/day was sufficient to eradicate pre-established tumors in mice. An expected approximate equivalent dose for administration to a human can be calculated using known formulas to be 20 mg/kg or 1.2 mg/day for a 60 kg adult and 2.0 mg/day for a 100 kg adult. Thus, the dose for systemic administration in a human the dose should be in the range of 0.1 mg/day to 20 mg/day.

The invention will now be illustrated by the following non-limiting Examples.

EXAMPLES

In the examples below, the vectors are described in abbreviated form.

Materials and Methods (i) Reagents and Assays.

Poly IC was obtained from Sigma (Rehovot, Israel). The molecular weight may vary from lot to lot with a range from 90,000 to 1,400,000 with an average of 200,000 to 500,000. Since a base-pair has the Mw of 680 Da, 90,000 Da=133 bp; 1,400,000 Da=2059 bp; 200,000 Da=294 bp; and 500,000 Da=735 bp (MW info taken from Sigma website). It was dissolved in diethylpyrocarbonate (DEPC)-treated double-distilled $H_2O$. The polyethylenimine (PEI), $PEI_{25}$, branched and succinimidyl 3-(2-pyridyldithio) propionate (SPDP) were purchased from Sigma-Aldrich (Munich, Germany). NHS-PEG-MAL (MW ¼ 3400) was obtained from Nektar Therapeutics (Huntsville, Ala., USA) and the recombinant mouse EGF (mEGF) from Pepro Tech EC Ltd. (London, UK). The PEI content of the conjugate was determined spectrophotometrically by TNBS assay at 405 nm. The amount of dithiopyridine linkers in PEI was determined after reduction of an aliquot with dithiothreitol (DTT) followed by absorption measurement of released pyridine-2-thione at 343 nm. The molar ratio of mEGF:dithiopyridine was determined spectrophotometrically at 280 and 340 nm. The amount of dithiopyridine was determined as described [6,7]. The yield of mEGF (mg) was calculated in two equations. Equation 1: $A_{280(a)}=A_{340}$ with DTT×5.1/8.1. Equation 2: $A_{280}$ revised=$A_{280}-A_{280(a)}$. The result of equation 2 was the amount of mEGF in mg. The Ellman assay was used for the determination of the mercapto groups in mEGF-SH. Liquid chromatography of conjugates was performed with the ÄKTA basic system from Amersham Biosciences (Little Chalfont, UK). Melittin (Mel) (D-Mel-SH; e280 ¼ 5570, MW ¼ 2893.6) was purchased from IRIS Biotech GmbH (Marktredwitz, Germany). All other chemicals including linear PEI, were purchased from Sigma-Aldrich.

pIC:Carrier Complex Components:

dsRNA in the form of a synthetic polyinosinic acid-polycytidylic acid complex (pIC) having RNA strands 100-300 ribonucleotides in length was obtained from Pharmacia-Amersham. For the preparation of the vectors, the polyIC is mixed with the conjugate MPPE, PPE or PEGE11 described herein. FuGENE6 transfection reagent was obtained from Roche. Covalently conjugated polyethylenimine (PEI)2s-poly(ethylene glycol) (PEG)-epidermal growth factor (EGF) and PEh-melittin (MEL) dsRNA carriers were synthesized as described below.

Preparation of Covalently Conjugated $PEI_{25}$-PEG-EGF Carrier (PPE)

General guidance for preparing covalently conjugated PEI2s-PEG-EGF carrier is provided in Current Protocols In Human Genetics, Supplement 11, Chapter: Vectors for Gene Therapy, 12.3.17; 12.3.18. John Wiley & Sons, Inc., 1996.

Reagents:

Branched PEI of average MW 25 kDa as determined via light scattering (PEhs) and SPDP were purchased from Sigma-Aldrich (Munich, Germany). N-hydroxysuccinimidyl polyethyleneglycol maleimide (NHS-PEG-MAL, MW=0.4 kDa) was obtained from Nektar Therapeutics. The compound NHS-PEG-MAL is used for conjugating moieties having a suitable reactive group to PEG. Recombinant mouse EGF was purchased from Pepro Tech EC Ltd. (London, UK).

Liquid Chromatography:

Liquid chromatography was performed using a Waters 626 pump and 996 diode array detector.

Quantitation of PEI:

The PEI content of conjugates was determined spectrophotometrically via 2,4,6-trinitrobenzenesulfonic acid (TNBS) assay at 405 nm as previously described (Snyder and Sobocinski, 1975. Anal. Biochem. 64, 284-288).

Determination of the Amount of Dithiopyridine Linkers:

The amount of dithiopyridine linkers which could be generated in $PEI_{25}$ for conjugations was determined after reduction of an aliquot with dithiothreitol (DTT) followed by absorption measurement of released pyridine-2-thione at 343 nm ($8=80801M$ cm).

Quantitation of Reactive Maleinimide Groups in NHS-PEG-MAL:

The amount of reactive maleinimide groups in NHS-PEG-MAL was calculated spectrophotometrically as a function of absorbance at 300 nm (A300). A solution of 1 mg/ml NHS-PEG-MAL in water has an OD300 of 0.15 for a 1 cm path length. The amount of the reactive maleinimide groups in the $PEI_{25}$-PEG-MAL conjugate were calculated similarly by the difference in A300 prior to and following addition of 10 microliters 1 molar DTT solution to 100 microliters of the sample (addition of DTT removes the A300 of the maleinimide group by electron delocalization).

Quantitation of EGF Concentration:

The concentration of soluble recombinant EGF was calculated by measuring the absorption of EGF in solution at 280 nm: a solution of 1 mg/ml EGF in water results in an OD of 3.1 (1 cm path length). The molar ratio of EGF and dithiopyridine in a EGF-PDP conjugate is determined spectrophotometrically at 280 and 340 nm. For the amount of dithiopyridine absorption is measured at 340 nm (see above). The initial absorption of the conjugate is measured at 280 nm (A280); to correct for the absorption of dithiopyridine at 280 nm, this value is corrected by following equations.

$$A280\ a = A340 \text{ with } DTT \times 5.1/8.1 \qquad \text{Equation 1}$$

$$A280 \text{ revised} = A280 - A280\ a \qquad \text{Equation 2}$$

The result of equation 2 is used to calculate the final concentration of EGF. An Ellman assay is used for the determination of the mercapto groups in EGF-SH.

Synthesis of $PEI_{25}$-PEG-MAL:

A 1.6 micromole aliquot of $PEI_{25}$ obtained by gel-filtration (Sephadex G-25, superfine; Amersham Biosciences) dissolved in 0.25 M NaCl was adjusted to pH 4.4 by careful addition of HCl. A 6.4 micromole aliquot of NHS-PEG-MAL dissolved in 0.4 ml water was added, and after 1 hour reaction at room temperature the salt concentration was adjusted to 1 M NaCl. This mixture was loaded on a cation-exchange column (Macro-prep High S; 10/10; BioRad, Munich, Germany) and fractioned using a salt gradient of 1-3 M NaCl in 20 mM sodium acetate, pH 4.5 with a flow rate of 0.5 ml/minute. Fractionation was performed using Buffer A (20 mM sodium acetate pH 4.5) and Buffer B (3 M NaCl, 20 mM sodium acetate pH 4.5), as follows: Time=0-15 minutes: 56% Buffer A, 44% Buffer B; Time=15-20 minutes: 44-100% Buffer B; Time=20-60 minutes: 100% Buffer B. The detector was set to 240 and 300 nm, and the product was eluted at Time=40-50 minutes. The molar ratio of $PEI_{25}$ and reactive maleinimide groups was 1:1.6.

Synthesis of EGF-PDP:

A 5 mg aliquot of EGF (MW=6 kDa) was dialyzed overnight against 20 mM HEPES pH 7.1 (degassed with argon). A 0.5 micromole aliquot of EGF and a 5 micromole aliquot of SPDP from a 10 mM stock in 100% ethanol were mixed. The concentration of ethanol in the mixture was approximately 33% (v/v). After 3 hours at room temperature the reaction mixture was loaded on a gel-filtration column (G-IO; 5 HRIO/30 column, Amersham Biosciences, Germany; 20 mM HEPES, pH 7.1 with 20% ethanol). The product (4 ml), detected at 300 nm, eluted at Time=18-26 min. The yield was 3.36 mg for EGF modified with 0.77 micromoles dithiopyridine.

Synthesis of EGF-SH:

A 0.56 micromolar aliquot of EGF was mixed with 50 equivalents of DTT in 100 microliters of water. After 5 minutes at room temperature, the reaction mixture was loaded on a gel-filtration column (G-10; HR10/30 column, Amersham Biosciences, Germany; 20 mM HEPES, pH 7.1 with 20% ethanol). The product (5.5 ml), detected at 280 nm, was eluted at Time=17-28 minutes. The molar ratio of EGF to —SH groups was 1:1.82.

Synthesis of $PEI_{25}$-PEG-EGF (PPE):

A 0.28 micromolar aliquot of EGF containing 0.51 micromoles of thiol groups was mixed under argon with PEI2s-PEG-MAL containing 0.51 micromoles of reactive maleinimide groups. The final pH of the reaction mixture was 6, and the final salt concentration was 0.3 M NaCl. After a 26 hour incubation at room temperature the salt concentration of the reaction mixture was adjusted to 0.5 M with 3 M NaCl, the reaction mixture was loaded on a cation-exchange column (Macro-prep High S; 1011 0; BioRad, Munich, Germany) and fractioned with a salt gradient of 0.5-3M NaCl in 20 mM HEPES, pH 7.1 using a flow rate of 0.5 ml/minute and the detector set at 280 nm. Fractionation was performed using Buffer A (20 mM HEPES pH 7.1) and Buffer B (20 mM HEPES pH 7.1, 3 M NaCl), as follows: Time=0-20 minutes: 78% Buffer A, 22% Buffer B; Time=20-80 minutes: 22-100% Buffer B; Time=80-90 minutes: 100% Buffer B. The conjugate was eluted at 2.4-3 M NaCl (10 ml pooled). Fractions (Time=10-28 minutes, product B) in the isocratic part were also pooled (9 ml). The product was dialyzed overnight at 4° C. against FIBS buffer (20 mM HEPES pH 7.1, 150 mM NaCl), pH 7.3 (degassed with argon). The amount of EGF in the conjugate (0.65 mg) and in product B (0.98 mg) was determined spectrophotometrically at 280 nm. The concentration of $PEI_{25}$ in the conjugate (136 nmol) and in product B (38 nmol) was determined spectrophotometrically by TNBS assay at 405 nm. The molar ratio of EGF to $PEI_{25}$ in the conjugate was 0.8:1.

Synthesis of Mel-$PEI_{25}$-PEG-mEGF.

mEGF-PEG-$PEI_{25}$ (83 nmol PEI) was mixed with SPDP (664 nmol in 100% ethanol) under argon. After 3 h at room temperature the mixture of about 2 ml was loaded on a gel filtration column (Sephadex G25 superfine; HR10/30; 20 mM HEPES [pH 7.1], 0.5M NaCl; Amersham Biosciences). The purified PDP (pyridyldithiopropionyl)-functionalized conjugate (5 ml) containing 309 nmol of PDP was concentrated to 1.5 ml by speed vacuum. For the reaction with melittin (Mel), 464 nmol of Mel was weighed out and dissolved in 0.5 ml of 0.5 M NaCl, 100 mM HEPES [pH 7.4] degassed with argon. Both components were mixed under argon. After 20 h at room temperature mEGF-PEG-$PEI_{25}$-Mel was purified by gel filtration. To gel filtrate the conjugate, a Superdex 75 prep grade column 10/30, conditioned with $PEI_{25}$ (10 mg $PEI_{25}$/60 ml gel material) was used. After dialysis overnight (MWCO 14000; Visking type 27/32; Roth, Karlsruhe, Germany) against HBS 6 ml of mEGF-PEG-$PEI_{25}$-Mel (MPPE) conjugate were obtained; these contained 66 nmol PEI (1.64 mg), 350 nmol Mel, and 70 nmol EGF.

Cells:

A431 (ATCC® No. CRL-1555™), MDA-MB-468 (ATCC® No. HTB-132™), U-138 MG (ATCC® No. HTB-16™), MCF7, MDA-MB-231 (ATCC® No. HTB-26™), U87MG (ATCC® No. HTB-14™), and U87MGwtEGFR cells.

PBMC Extraction.

PBMCs from healthy human donors were separated on Ficoll Plaque (Pharmacia), washed twice with 50 ml RPMI 1640 medium, resuspended at a density of $4 \times 10^6$/ml and cultured in this medium supplemented with 10% fetal calf serum, 100 units/ml penicillin, 100 µg/ml streptomycin.

Cytokine Measurements:

Gro-α, IP-10, IFN-β, IFN-γ, IL-2, TNF-α were measured using cytokine specific ELISA (Biosource, Inc).

Expression of Cytokines in Tumors and Blood.

Cells were s.c. injected into right (A431 or MDA-MB-468) and left (U138MG) flanks of SCID/NOD mice. 17 days later, when the tumors reached approx. 100 mm$^3$, treatment was initiated as follows: 3 consecutive PolyIC/MPPE I.V. injections of 5 µg/mouse/day. 24 hrs after the last PolyIC/MPPE injection, 4 million fresh PBMCs were injected I.P. 48 hrs later tumors were extracted, homogenized with 1.5 mL extraction buffer (containing 10 mM Tris pH 7.4, 150 mM NaCl, 1% Triton X-100) per gram of tissue, using a homogenizer. Homogenates were centrifuged at 13,000×g for 10 minutes at 4° C., stored at −70° C., then subjected to ELISAs. ELISAs were also performed on blood samples taken 24 hrs after the last PolyIC/MPPE injection ("Blood 3d") and 48 hrs after PBMC injection ("Blood"). The numbers shows pg of cytokine per 1 gram of tissue (1 ml of blood=1 gr)

PBMC-Mediated Bystander Effect.

100,000 MDA-MB-468 cells or A431 cells were seeded into 6-well plates and grown overnight with 2 ml medium per well (2). Cells were then transfected with Poly IC/MPPE, to a final concentration of 0.1 or 0.5 µg/ml. 48 hrs after transfection 0.5 ml of medium from the transfected cells ("conditioned medium") was added to 500,000 PBMCs which had been seeded 24 hrs earlier into 24-well plates and grown in 0.5 ml medium. 0.1 ml of medium from the challenged PBMCs was then exchanged for 0.1 ml medium from additional non-transfected MDA-MB-468 cells and U138MG cells ("indicator cells") seeded on 96-well plates 24 hrs earlier. Survival of these cells was determined by methylene blue assay (2), 48 hours after challenge with the medium from the PBMCs.

In parallel, to show the direct bystander effect, 0.1 ml of conditioned medium was used to replace 0.1 ml medium from non-transfected indicator cells seeded 24 hrs earlier onto 96-well plates and grown in 0.2 ml medium. Survival of these cells was determined 48 hours after addition of the conditioned medium using methylene blue.

In Vitro Cancer Cell Killing by Activated PBMCs.

20,000 A431, 30,000 MDA-MB-468 or 20,000 U138MG cells were seeded onto 24-well plates and grown overnight in 1 ml RPMI medium supplemented with 10% FCS and antibiotics. Cells were then transfected with PolyIC/MPPE at 0.1 mg/ml. 24 hrs later 500,000 PBMCs/well were added to the cancer cells and co-incubated for another 24 hrs. Apoptotic cells (red fluorescence) were visualized using an Annexin-V-Biotin kit (Biosource, Inc.). To distinguish tumor cells from PBMCs, tumor cells were labeled with FITC-conjugated EGFR antibody (Biosource, Inc., green fluorescence). Cells were visualized with a fluorescent microscope and photographed using a digital camera.

Effect of PolyIC/MPPE/PBMC Treatment on Survival of Mice with Disseminated Tumors.

Female SCID-NOD mice (Harlan), were injected IV with 1 million A431 or MDA-MB-468 cells suspended in 200 µl PBS. 10 or 15 days later, the animals were randomly divided into groups (5 mice per group) and treatment was initiated with a series of intravenous injections of 20 μg polyIC/MPPE. 24 hrs after the last PolyIC injection, the animals were injected once with four million PBMCs.

Example 1

PolyIC/MPPE Induces Expression of Immunoactive Cytokines in A431 and MDA-MB-468 Cells In our previous study (2) we showed that a low dose of EGFR-targeted PolyIC induced expression of IFN-α, IP-10 and Gro-α in EGFR overexpressing glioblastoma cells (U87MGwtEGFR), but not in cells with low levels of EGFR (U87MG). These data support the notion that cells produce these cytokines only when a certain threshold level of dsRNA has been internalized, and that this dose is achieved only in cells overexpressing EGFR. In this study we extended the analysis to two additional EGFR overexpressing cancer cell lines: A431 (vulval carcinoma) and MDA-MB-468 (breast carcinoma). When these cells were transfected with PolyIC/MPPE (2.5 μg/ml), we detected up to 5.1 pg/ml of IFN-13; 148 pg/ml of Gro-α and 188 pg/ml of IP-10 (Table 2). Gro-α and IP-10 are chemokines responsible for the recruitment of T cells to the area where they are expressed. Thus, A431 and MDA-MB-468 cells, like U87MGwtEGFR cells, secrete cytokines into the medium, following challenge with PolyIC/MPPE.

TABLE 2

Expression of cytokines in the medium of poly IC/MPPE transfected cells

|  | A431 |  | MDA-M-468 |  |
| --- | --- | --- | --- | --- |
| poly IC/MPPE | − | + | − | + |
| IFN-β (pg/ml) | 0 | 5.1 | 0 | 4.1 |
| Gro-α (pg/ml) | 14 | 148 | 0 | 121 |
| IP-10 (pg/ml) | 23 | 188 | 20 | 138 |

Example 2

In Vitro Activation of Human Immune Cells

Given the above results, we hypothesized that the cytokine-enriched medium from A431 and MDA-MB-468 cells treated with PolyIC/MPPE should stimulate the immune system. We examined whether this was so, by testing the effect of medium from PolyIC-transfected cancer cells on healthy human peripheral blood mononuclear cells (PBMCs). PBMCs consist of several types of immune cells (NK, T-cells, NK-T cells, macrophages). When activated, these cells produce toxic cytokines, such as IFN-γ and TNF-α, known to be effective against various cancer cells. PBMCs also interact with each other, leading to a synergistic, highly anti-proliferative effect. For example, activated T cells and NK cells produce IFN-γ, which activates macrophages and stimulates the production of TNF-α. Release of IL-2 into the medium correlates directly with PBMC activation and can be conveniently quantified by ELISA. Thus PBMCs are a convenient system for studying the selective immune reaction against PolyIC-transfected tumor cells.

Figure 1B:
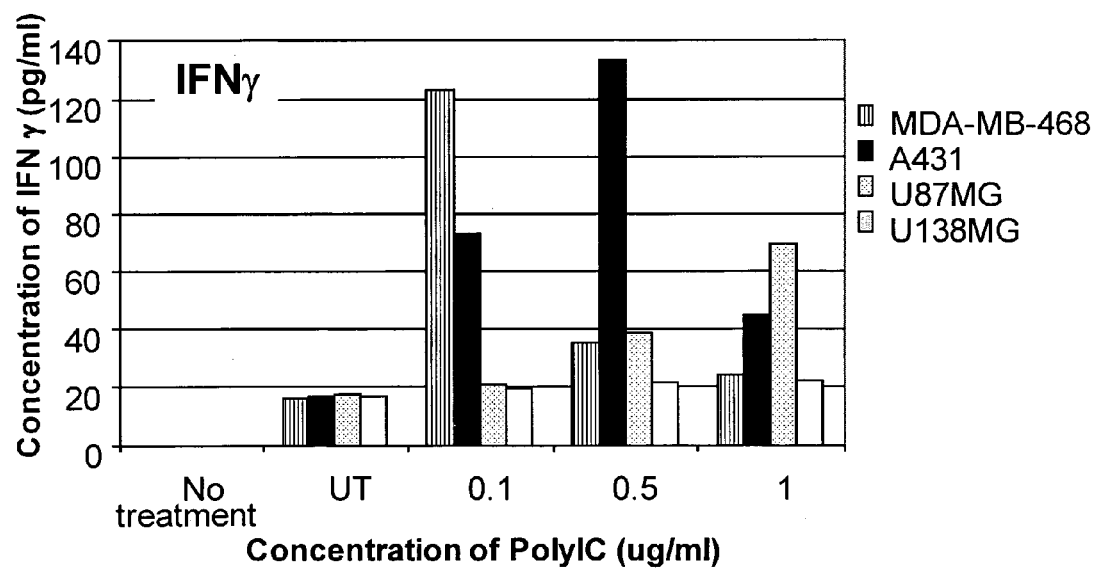
Figure 1C:
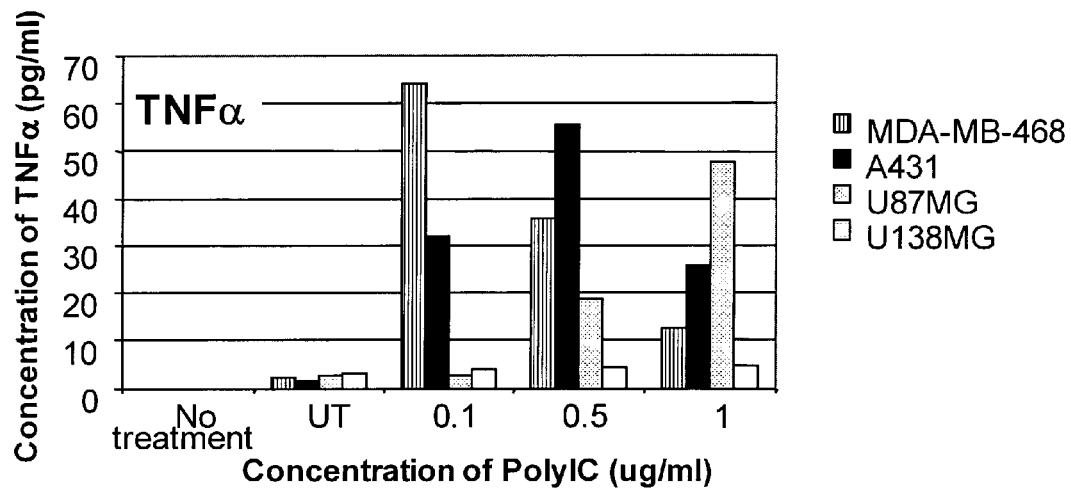
Figure 2A:
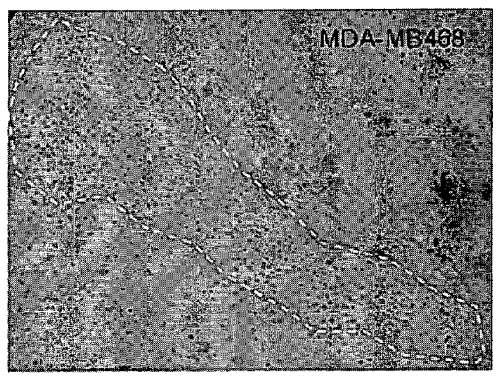
FIGS. 2A-D show that immune cells infiltrate into PolyIC/MPPE+PBMC treated EGFR overexpressing tumors, but not in U138MG cells (no EGFR expression). A431 (2A) or MDA-MB-468 (2B) cells were injected subcutaneously (s.c.) into the right flank and U138MG (2C-2D) was injected into the left flank of SCID-NOD mice (compare FIG. 2A with FIG. 2C, and FIG. 2B with FIG. 2D). When the tumors reached approx 100 mm$^3$ the treatment was initiated with 3 consecutive PolyIC/MPPE I.V. injections of 5 µg/mouse/day. 24 hrs after the last PolyIC/MPPE injection 3 million PBMCs were injected I.P. 24 hrs later tumors were extracted, and fixed in 4% formalin. Paraffin sections were then prepared, stained with H&E and subjected to histopathological analysis. Dashed lines show areas of immune cell infiltration.
Figure 2B:
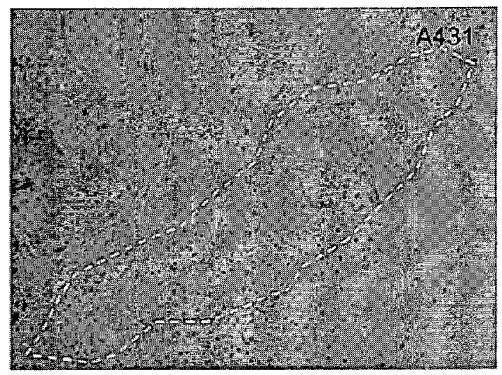
Figure 2C:
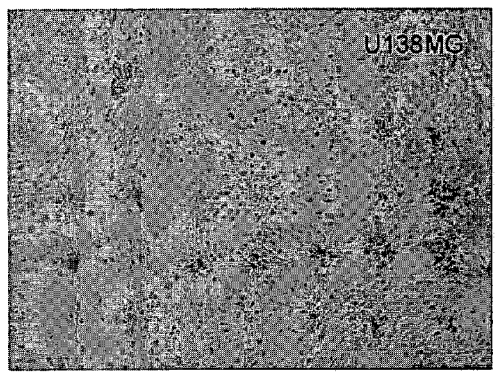
Figure 2D:
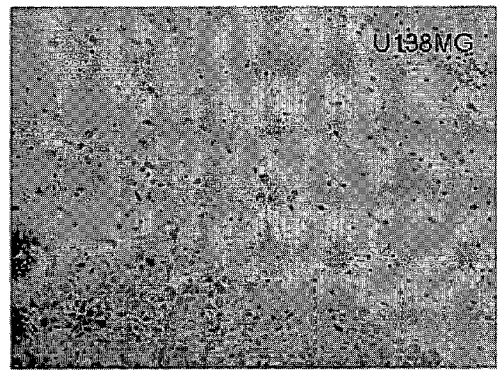

PBMCs were challenged with medium from PolyIC/MPPE-transfected cancer cells. For this purpose, 500,000 PBMCs were seeded into 24 well plates and grown overnight in 0.5 ml medium as described in Methods. The PBMCs were then challenged with 0.5 ml of medium removed from A431, MDA-MB-468, U87MG or U138MG cells transfected with PolyIC/PEI-PEG-EGF+PEI-Mel 48 hrs after transfection. The PBMC medium was collected 24 and 48 hours after the challenge and IFN-γ, IL-2 and TNF-α were measured using ELISA assays. FIG. 1A shows the induction of IL-2 expression by PBMCs, 24 and 48 hrs after the challenge. Medium from A431 and MDA-MB-468 cells transfected with PolyIC/MPPE (0.1 μg/ml) led the PBMCs to produce up to 165 pg/ml of IL-2. In contrast, medium from PolyIC/MPPE-treated U87MG cells (with ~12 times lower expression of EGFR than A431 and MDA-MB-468 cells) or U138MG cells (no EGFR expression) did not affect PBMCs. Similar results were obtained when the expression of other cytokines was examined: Both IFN-γ (FIG. 1B) and TNF-α (FIG. 1C) were induced in PBMCs challenged with the medium from PolyIC/MPPE-transfected A431 and MDA-MB-468 cells, but not from PolyIC/MPPE-transfected U87MG and U138MG cells transfected with 0.1 μg/ml of PolyIC/MPPE.

Example 3

Activation of PBMCs In Vivo

Expression of these cytokines selectively in EGFR overexpressing tumors was also confirmed in vivo (Table 3). SCID-NOD mice bearing EGFR overexpressing subcutaneous tumors on the right flank and U138MG tumors on the left flank were intravenously treated with 4 consecutive daily injections of PolyIC?MPPE followed by a single intraperitoneal injection of four million PMBCs. Expression of and, at much higher concentrations, in the EGFR overexpressing tumors (Table 3). These cytokines were expected to attract PMBCs selectively to the EGFR overexpressing tumors, where the PMBCs would be activated.

TABLE 3

In vivo cytokine expression pattern

| MDA-MB-468 | | | | | | | | | | | | |
| --- | --- | --- | --- | --- | --- | --- | --- | --- | --- | --- | --- | --- |
|  | IP10 | | Gro-α | | IF | | IL2 | | IFNγ | | TNFα | |
| PolyIC/MPPE/PBMC | − | + | − | + | − | + | − | + | − | + | − | + |
| MDA-MB-468 | 0 | 218 | 201 | 442 | 0 | 4 | 0 | 151 | 0 | 24 | 0 | 0.89 |
| U138MG | 0 | 46 | 322 | 360 | 0 | 0 | 0 | 33 | 0 | 0 | 0 | 0 |
| Blood | 12 | 81 | 45 | 225 | 0 | 0 | 0 | 52 | 0 | 2 | 0 | 0 |
| Blood 3 days | 11 | 89 | 52 | 203 | 0 | 0 | — | — | — | — | — | — |
| A431 | | | | | | | | | | | | |
|  | IP10 | | Gro-α | | IFNβ | | IL2 | | IFNγ | | TNFα | |
| PolyIC/MPPE/PBMC | − | + | − | + | − | + | − | + | − | + | − | + |
| A413 | 16 | 346 | 411 | 870 | 0 | 12 | 0 | 112 | 0 | 38 | 0 | 0.74 |
| U138MG | 0 | 66 | 240 | 410 | 0 | 0 | 0 | 18 | 0 | 0 | 0 | 0 |
| Blood | 22 | 99 | 63 | 263 | 0 | 0 | 0 | 37 | 0 | 6 | 0 | 0.12 |
| Blood 3 days | 34 | 70 | 44 | 294 | 0 | 3 | — | — | — | — | — | — |

We then asked the question whether the concentration of the cytokines at the vector-transfected EGFR overexpressing tumors is high enough to actually attract and activate immune cells. In a separate experiment, cells were injected s.c. into the right (A431 or MDA-MB-468) and left (U138MG) flanks of SCID-NOD mice. When the tumors reached approx 100 mm³ the treatment was initiated with 3 consecutive PolyIC/MPPE I.V. injections of 5 μg/mouse/day. 24 hrs after the last PolyIC/

MPPE injection, 3 million PBMCs were injected I.P. 24 hrs later tumors were extracted, and fixed in 4% formalin. Paraffin sections were then prepared, stained with H&E and subjected to histopathological analysis. Dashed lines in FIG. 2 show areas of immune cell infiltration in which infiltration of the PBMCs into the EGFR overexpressing tumors of the PolyIC/+PBMCs treated animals was detected. No immune cell infiltration was detected in U138MG tumors, which do not overexpress EGFR.

PolyIC/+PBMCs treated animals was detected. No immune cell infiltration was detected in U138MG tumors, which do not overexpress EGFR.

Example 4

PBMC-Mediated Bystander Effect

Figure 3A:
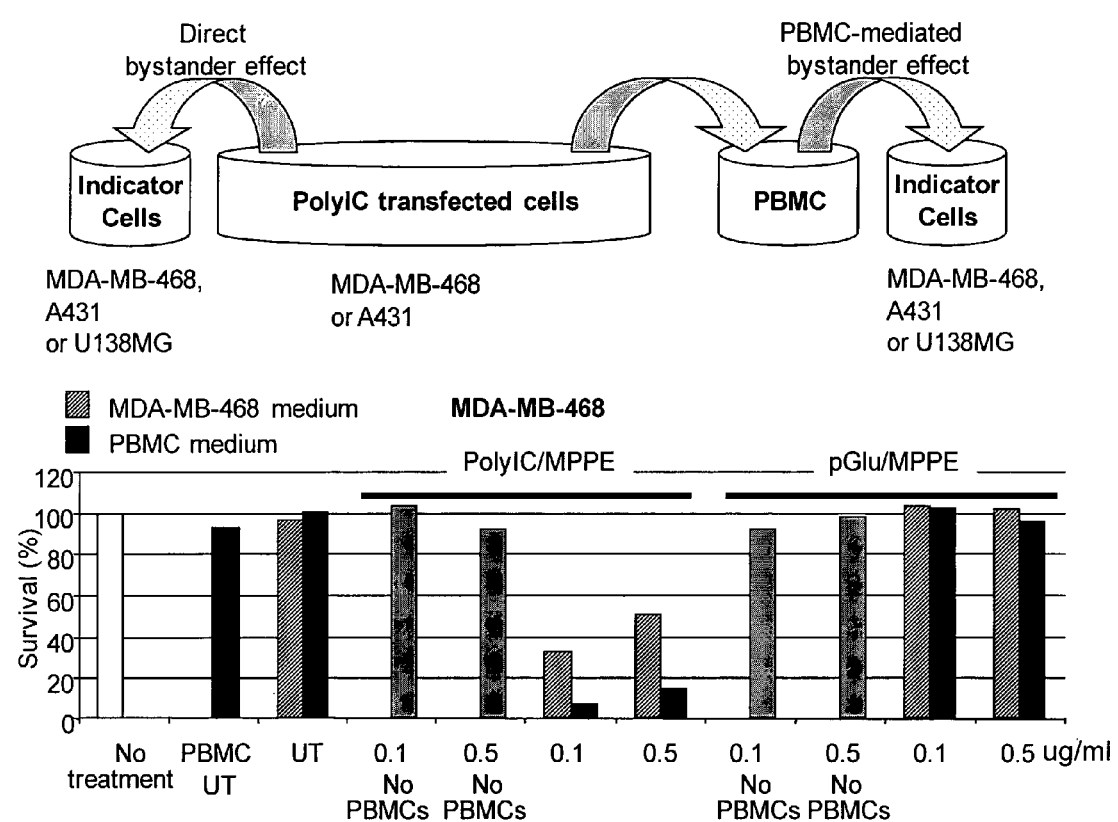
FIGS. 3A-D show PBMC-mediated bystander effect.
Figure 3B:
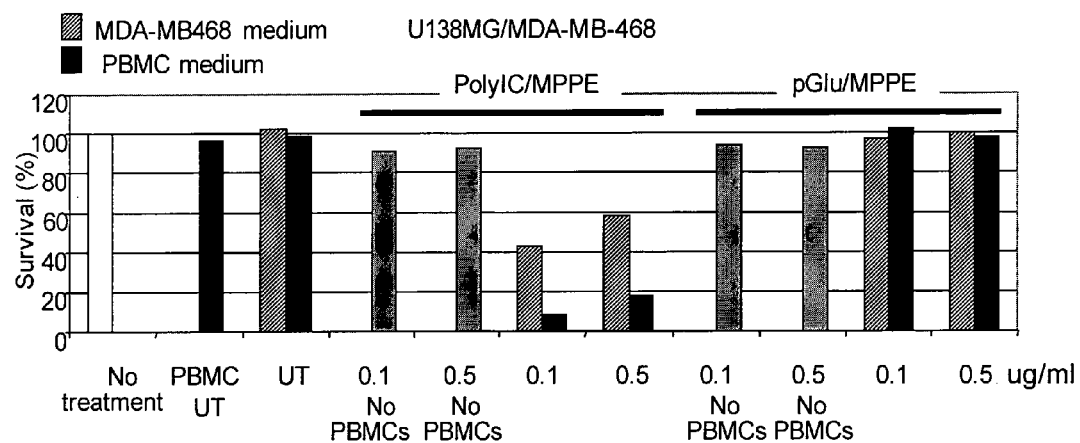
Figure 3C:
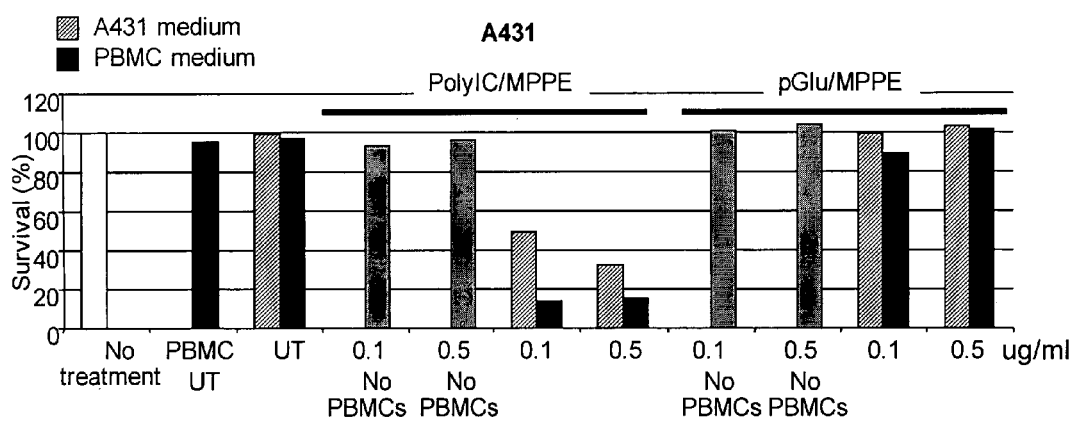
Figure 3D:
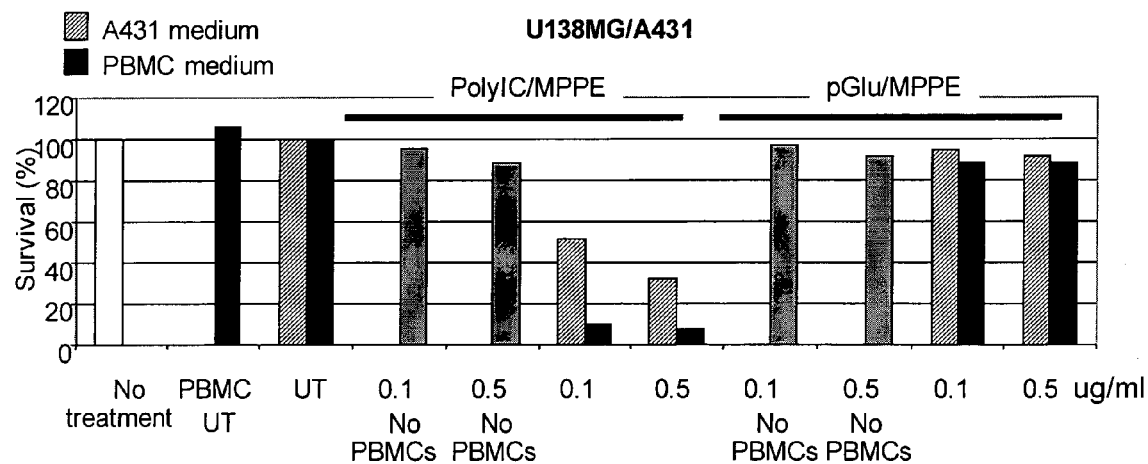

Expression of IFN-γ and TNF-α, potent antitumor cytokines, mediate direct bystander killing of untransfected cancer cells. The question is then, if the level of cytokines is high enough, not only to attract immune cells, but also to activate them. In order to examine PBMC-mediated bystander effects, A431 or MDA-MB-468 cells were first transfected with PolyIC/MPPE and 48 hrs later PBMCs were challenged with the medium from the transfected cells (Methods). After another 48 hrs, medium from the challenged PBMCs was added to newly seeded, non-transfected cells (FIG. 3). The PBMC-mediated bystander effect was examined 24 and 48 hrs after medium exchange and compared with the "direct" bystander effect, mediated by medium from PolyIC/MPPE-treated A431 and MDA-MB-468 cells (FIGS. 3A and 3C). Both direct and PBMC-mediated bystander effects are clearly shown in FIG. 3. The PBMC-mediated effect was particularly strong, killing up to 90% of the non-transfected cells. U138MG cells, which do not express EGFR at all, were also efficiently inhibited by both types of medium (FIGS. 3B and 3D). No effect was observed when pIC was replaced by polyglutamic acid (pGlu), which similarly forms particles with MPPE but does not induce an immune response. These results suggested that the combination of PolyIC/MPPE and PBMC would synergize to effectively kill cancer cells.

Example 5

PBMCs Strongly Enhance PolyIC/MPPE Cancer Cell Killing In Vitro

Figure 4A:
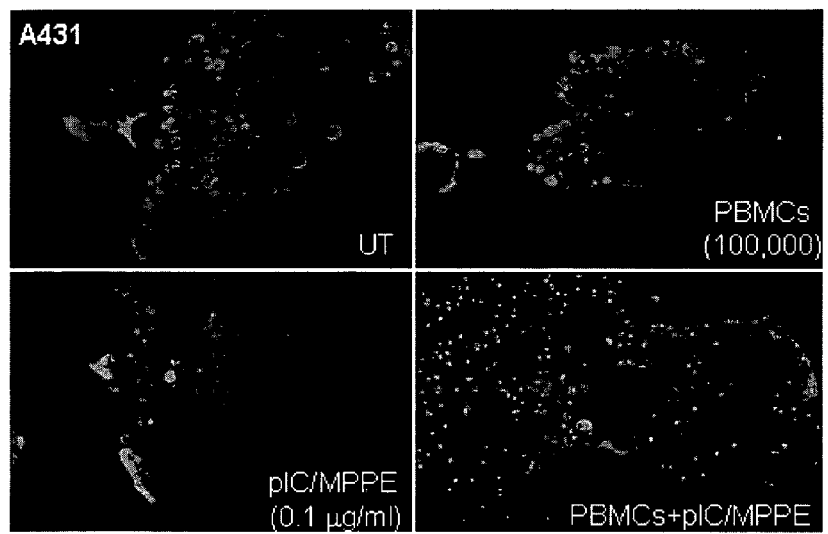
FIGS. 4A-C show in vitro cancer cell killing by activated PBMCs. Cells were grown as described in Methods. Cells were then transfected with PolyIC/MPPE at 0.1 µg/ml. 24 hrs later 500,000 PBMCs/well were added to the cancer cells and co-incubated for another 24 hrs. Apoptotic cells (bright dots) were visualized using an Annexin-V-Biotin kit (Biosource, Inc.). To distinguish tumor cells from PBMCs, tumor cells were labeled with FITC-conjugated EGFR antibody (Biosource, Inc., grey cells). Cells were visualized with a fluorescent microscope and photographed using a digital camera: A431 cells, MDA-MB-468 cells, and U138MG cells are shown in FIGS. 4A, 4B and 4C, respectively.
Figure 4B:
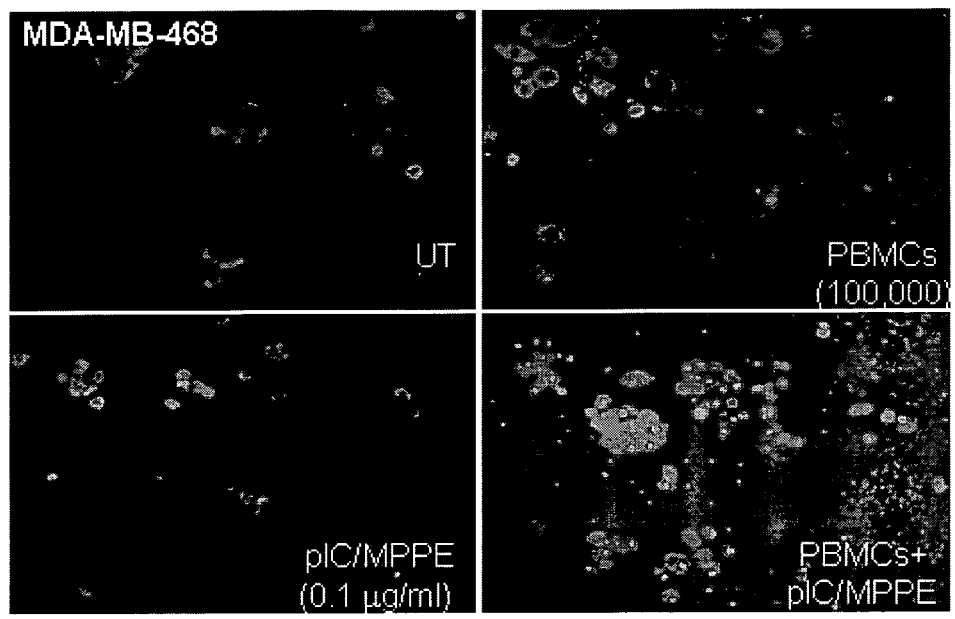
Figure 4C:

To examine the synergistic cancer killing effect, tumor cells (grown as described in Methods) were transfected with PolyIC/MPPE at low dose (0.1 μg/ml). 24 hrs later, 500,000 PBMCs/well were added to the cancer cells and co-incubated for another 24 hrs followed by addition of PBMCs (FIG. 4). To distinguish tumor cells from PBMCs, tumor cells were labeled with FITC-conjugated EGFR antibody (Green fluorescence). Tumor cells undergoing apoptosis were detected with an Annexin-V-Biotin kit, Biosource Inc. (Red fluorescence). Cells treated with either PolyIC/MPPE alone or PBMCs alone showed a very weak apoptotic signal. In contrast, a strong apoptotic signal was obtained when the EGFR overexpressing cells were treated with both PolyIC/MPPE and PBMCs (FIG. 4A, B). U138MG cells did riot undergo detectable apoptosis (FIG. 4C). Thus, the addition of PBMCs to PolyIC/MPPE-treated tumor cells strongly enhanced tumor cell apoptosis.

Example 6

Figure 5A:
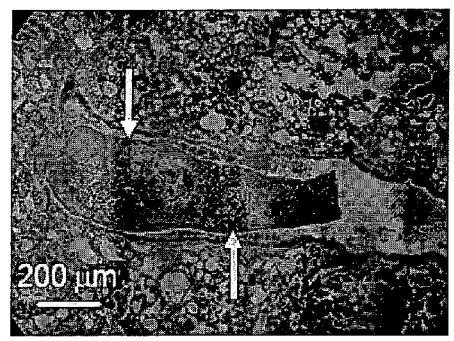
FIGS. 5A-E show effect of PolyIC/MPPE/PBMC treatment on survival of mice with disseminated tumors. Disseminated tumors were established as described in Methods. (5A) Histopathological analysis of mouse lungs at the time of treatment initiation (15 days after cell injection). Arrows point to a tumor in a lung capillary. (5B, 5C) 15 days after cell injection the animals were randomly divided into groups (5 mice per group) and the treatment was initiated with 4 consecutive intravenous injections of 20 µg polyIC/MPPE at 24 hr intervals. 24 hrs after the last PolyIC injection, the animals were injected once with four million PBMCs. (5B) Shows survival of animals with A431 tumors. (5C) Shows survival of animals with MDA-MB-468 tumors. pGlu/MPPE, Poly Glutamic acid/MPPE; UT, Untreated. (5D, 5E) 10 days after cell injection the animals were randomly divided into groups (5 mice per group) and the treatment was initiated with 3 cycles of 3 or 4 consecutive intravenous injections of 20 µg polyIC/MPPE at 24 hr intervals (total 10 injections). The interval between cycles was 48 hrs. This procedure eliminated toxic effects of the treatment like weight loss (data not shown). Control groups included mice treated with pGlu/MPPE (Poly Glutamic acid/MPPE) to determine the effect of the conjugate without PolyIC and HBG buffer (Hepes-buffered Glucose)(2). (5D) Shows survival of animals with A431 tumors. (E) Shows survival of animals with MDA-MB-468 tumors. UT, Untreated.
Figure 5B:
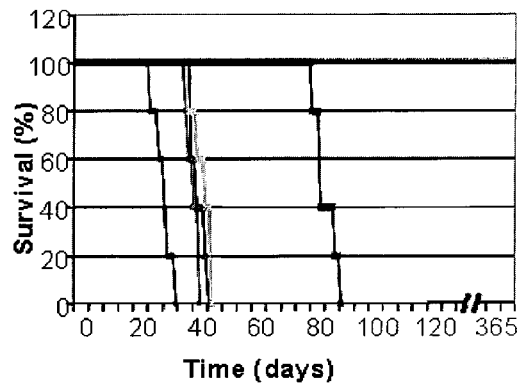
Figure 5C:
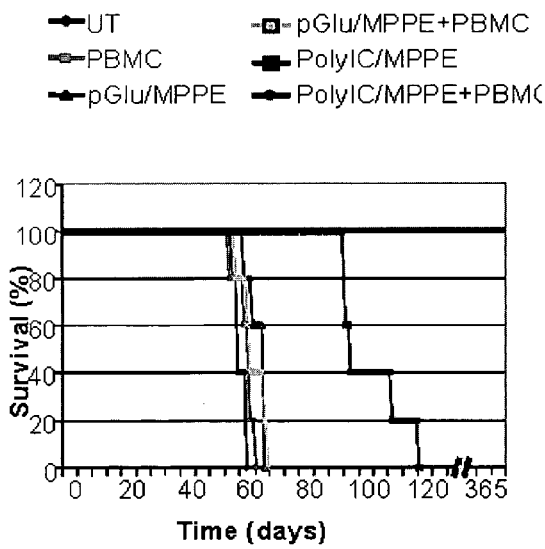
Figure 5D:
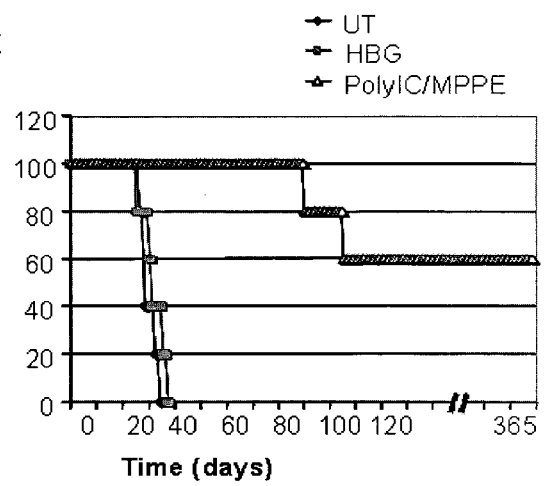
Figure 5E:
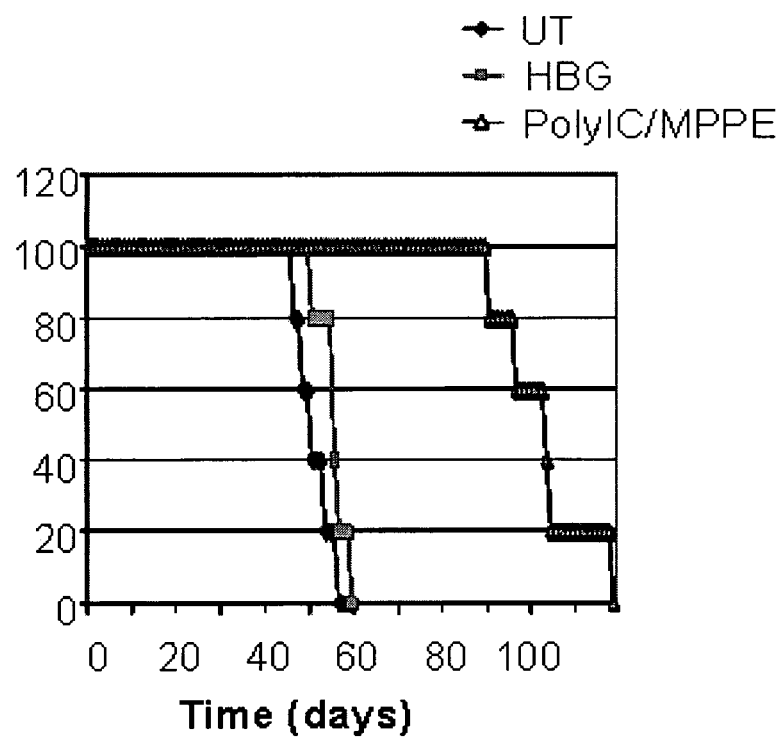

Systemic Application of PolyIC/MPPE Combined with PBMCs Cures Mice with Disseminated Tumors In view of our earlier finding that the PolyIC-loaded EGFR homing vector had no toxic effects on normal brain cells in tissue culture or in vivo (Shir et al., 2006), we examined whether EGFR-targeted PolyIC/MPPE could be applied systemically, for the treatment of disseminated EGFR overexpressing tumors in vivo. In the absence of a mouse model of EGFR overexpressing tumors, we injected i.v. 2 million human A431 or MDA-MB-468 cells into SCID-NOD mice as described in Methods. Ten days after cell injection, treatment was initiated, with two 3-day cycles and one 4-day cycle of daily injections of 20 μg PolyIC/MPPE, with a 24 hour interval between each cycle (i.e. a total of 10 injections, spread over 12 days). This procedure eliminated toxic effects of the treatment like weight loss (data not shown. Mice bearing A431 tumors that received PolyIC/MPPE survived at least 3 times longer than untreated mice, and three mice were completely cured (FIG. 5D). Mice bearing MDA-MB-468 tumors treated with PolyIC/MPPE survived up to twice as long as untreated mice (FIG. 5E).

These results, combined with the finding that PBMCs strongly enhance the effect of PolyIC/MPPE in vitro, encouraged us to test whether PBMCs would similarly enhance the effect of PolyIC/MPPE in vivo. For these experiments, we waited 15 days after injection of A431 or MDA-MB-468 cells in SCID-NOD mice, at which point large tumors of up to 500 μm could be detected in the lungs (FIG. 5). The mice were then treated with 4 consecutive, daily intravenous injections of 20 μg of PolyIC/MPPE. Control groups included mice treated with pGlu/MPPE (Poly Glutamic acid/MPPE) to determine the effect of the conjugate without PolyIC. 24 hrs after the final PolyIC injection, the mice were injected once with four million human PBMC. "Reconstitution" of the SCID-NOD mouse immune system using human PBMCs is a common practice. As in the earlier experiment, PolyIC-MPPE treated mice bearing A431 tumors survived longer than untreated mice. Mice that were treated with both PolyIC-MPPE and human PBMCs survived for more than a year, and did not show any signs of tumors (FIG. 5B). Similarly, mice bearing MDA-MB-468 tumors treated with PolyIC/MPPE alone survived up to twice as long as untreated mice, whereas mice treated with both PolyIC/MPPE and PBMCs survived more than a year and did not show any signs of tumors (FIG. 5C). No significant toxicity, reduction in weight or abnormal behavior was observed either during the treatment or afterwards. Thus, by introducing human PBMCs, we were able to significantly reduce the dosage of PolyIC/MPPE and to eliminate established disseminated tumors. Hence, PBMCs play a crucial role in tumor eradication.

Example 7

Comparison of the Second Generation Vectors with the First Generation Vectors

The advanced second-generation vectors provided by the present invention, herein designated pIC/$P_{221}$PE and pIC/$P_{221}$PGE11, are composed of PolyIC complexed with the conjugates $P_{221}$PE and $P_{221}$PGE11, respectively. These conjugates comprise linear polyethyleneimine, PEG and EGF or the peptide GE11, instead of the branched polyethyleneimine in the conjugate MPPE of the first generation vectors, and are significantly simpler to produce, can be made in larger and more uniform batches, and the resulting vectors exhibit improved cancer cell killing activity than the first generation vectors.

7.1 Preparation of the New Conjugates $P_{221}PE$ and $P_{221}PGE11$

For the synthesis of the novel conjugates, bifunctional PEG (NHS-PEG2k-OPSS, from Nektar Therapeutics, USA) was used; it PEGylates linear PEI at one end and couples with HS-mEGF or HS-GE11 at the distal end via the OPSS (orthopyridyl disulfide) moiety via a disulfide bridge. This simple two step procedure avoids the tedious purification regime applied for the synthesis of MPPE (see Methods, item (ii), hereinabove), resulting in a much higher overall yield.

The peptide GE11 can be synthesized either by recombinant methods well known in the art or it may be synthesized using well known chemical synthesis techniques, e.g. by using an automated synthesizer (available from e.g. Applied Biosystems, Germany) e.g. by using the company's protocols for t-butyloxycarbonyl (t-Boc) technique. The purification can be done by reverse-phase HPLC.

The vectors $pIC/P_{221}PE$ (pIC/PPE) and $pIC/P_{221}PGE11$ (pIC.PPGE) are obtained by mixing polyIC with the conjugate PPE or PPGE11.

7.2 Comparison of First- and Second-Generation Vectors In Vitro.

Since the sensitivity of the cells to the vectors of the invention is a function of their level of EGFR expression, it was interesting to assess the capability of the different vectors for killing cells having various levels of EGFR expression. For this purpose, 3000 cells of U138MG and 4000 cells of each of the other cell lines shown in Table 4, were seeded into 96-well plates and grown overnight. Cells were then transfected with pIC formulated with the indicated conjugate. Survival of the cells was analyzed by Methylene blue assay 48 hrs after transfection. Table 4 shows the cells used and the level of EGFR expression:

TABLE 4

Cell lines used and their level of EGFR expression

| Cell line | EGF receptor molecules/cell |
|---|---|
| U138MG | — |
| MCF7 | $0.8\text{-}5 \times 10^3$ |
| U87MG | $1 \times 10^5$ |
| MDA-MB-231 (MDA231) | $3\text{-}7 \times 10^5$ |
| U87MGwtEGFR | $1 \times 10^6$ |
| MDA-MB-468 (MDA468) | $2 \times 10^6$ |

Figure 6:
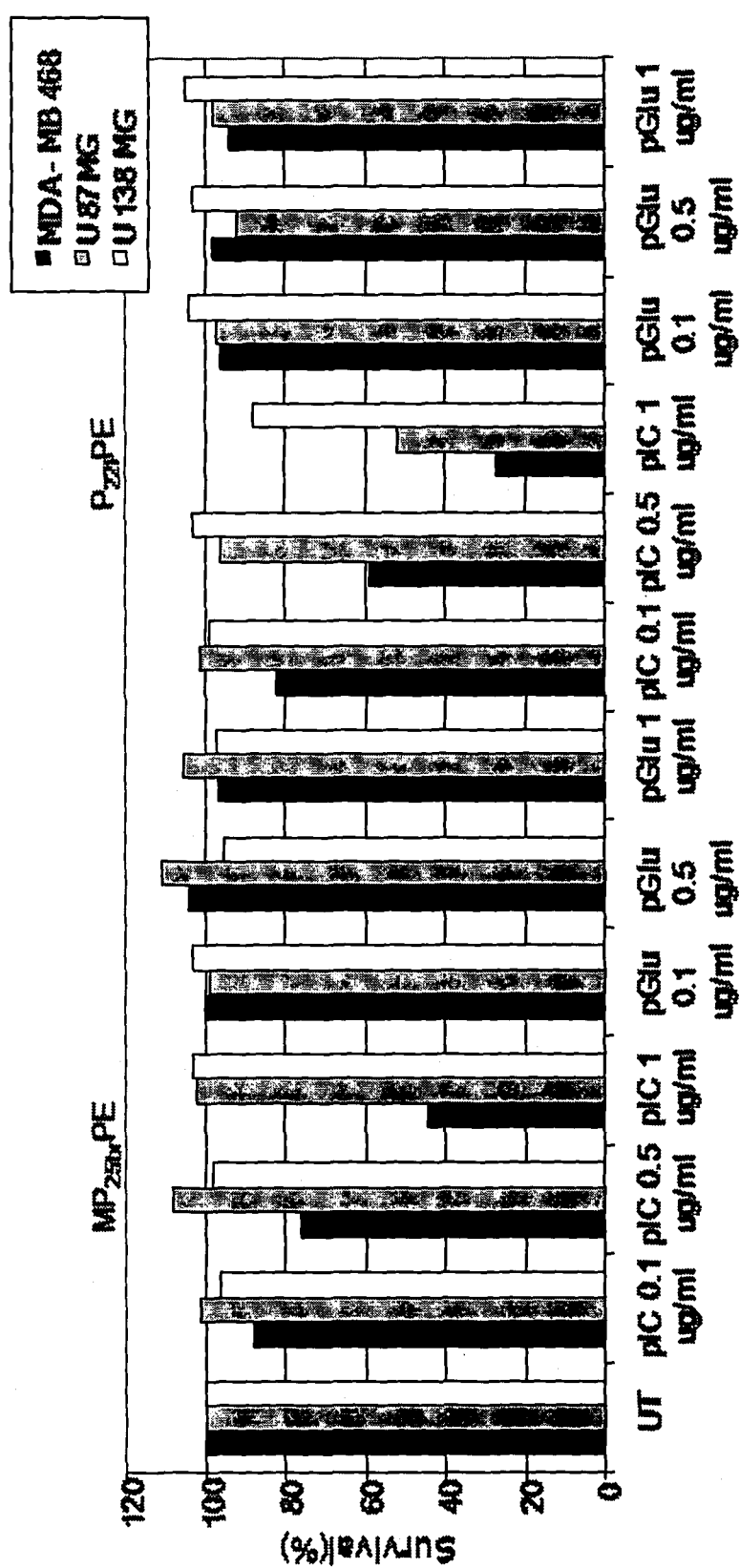
FIG. 6 depicts the effect of the vectors pIC/MPPE and pIC/PPE on survival of cells transfected therewith. The cells used were U87MG and MDA-MB468 (4000 cells of each), that express different levels of EGFR (U87MG express $1\times10^5$ EGFR; MDA-MB468 express $2\times10^6$ EGFR) and U138MG (3000 cells) that do not express EGFR. The cells were seeded into 96-well plates and grown overnight. Cells were then transfected with pIC formulated with the conjugate $MP_{25B}PE$ or $P_{221}PE$. Survival of the cells was analyzed by methylene blue assay 48 hrs after transfection. UT, untreated cells. pGlu, polyglutamic acid treated cells.

As can be seen in FIG. 6, the novel second-generation vector $pIC/P_{221}PE$ has somewhat stronger effect on cells with high expression of EGFR (MDA-MB-468) and significantly stronger effect on cells with lower expression of EGFR (U87MG) than the first-generation vector pIC/MPPE. Thus, $pIC/P_{221}PE$ should be significantly more beneficial on tumors with relatively lower expression of EGFR.

7.3 Comparison of PPE with PPGE11 In Vitro.

Figure 7:
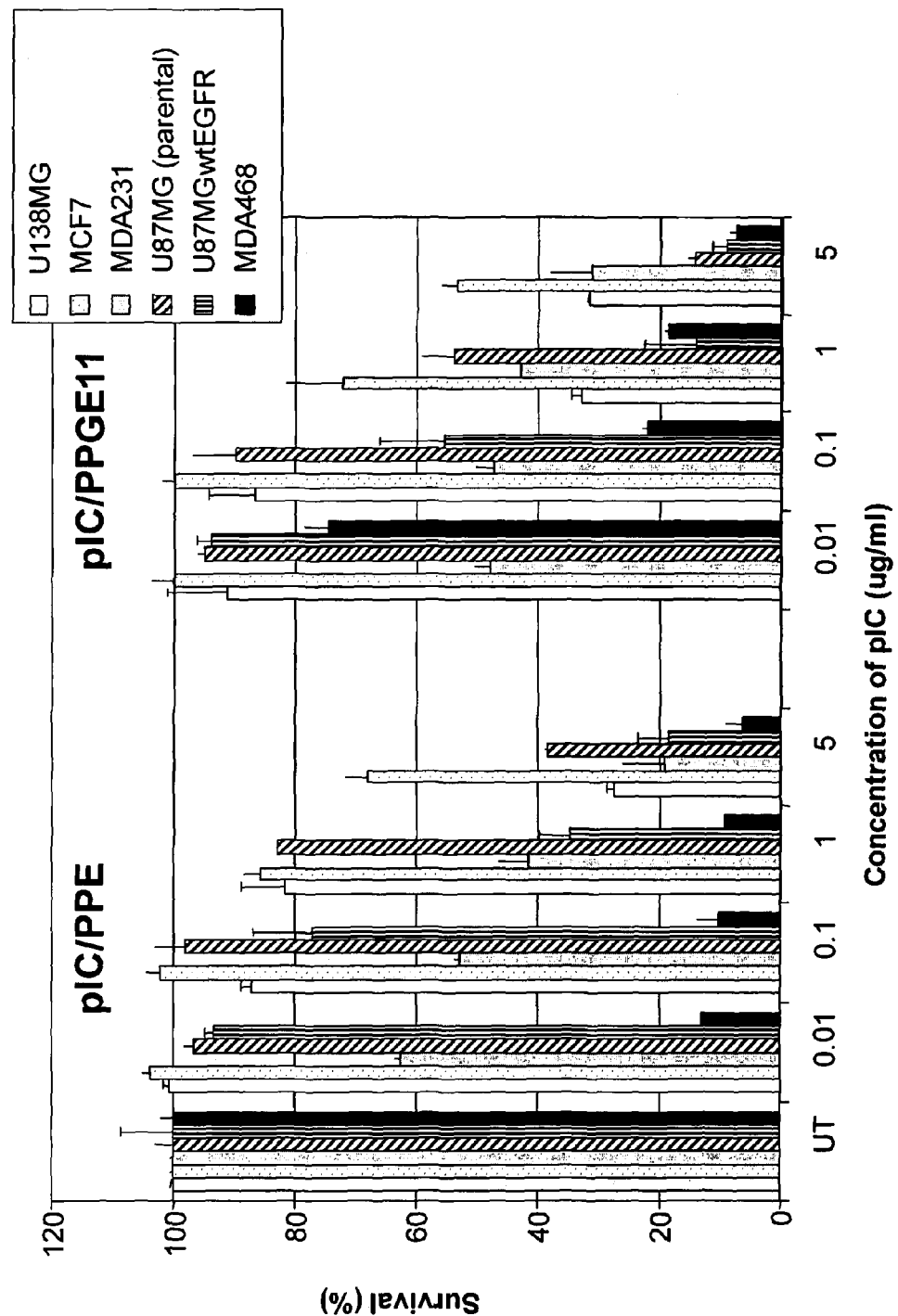
FIG. 7 depicts the effect of the vectors pIC/PPE and pIC/PPGE11 on survival of cells transfected therewith. The cells used were MCF7, MDA-MB231 (MDA231), U87MG, U87MGwtEGFR, and MDA-MB468 (MDA468) (4000 cells of each), that express different levels of EGFR (MDA231 express $3-7\times10^5$, U87MG express $1\times10^5$ EGFR; MDA468 express $2\times10^6$ EGFR) and U138MG (3000 cells) that do not express EGFR. The cells were seeded into 96-well plates and grown overnight. Cells were then transfected with pIC formulated with the conjugate $P_{251}PE$ or $P_{251}PGE11$. Survival of the cells was analyzed by methylene blue assay 48 hrs after transfection. UT, untreated cells.

The cell-killing capability of the vector $pIC/P_{221}PGE11$, having an EGFR binding peptide instead of EGF as the targeting moiety, was compared with that of $pIC/P_{221}PE$. As seen in FIG. 7, $P_{221}PE$ was highly efficient, killing up to 90% of MDA-MB-468 cells at just 0.01 μg/ml of pIC. No effect was observed on cells with low or no expression of EGFR at this concentration of pIC. $pIC/P_{221}PGE11$ was somewhat less efficient. Still, up to 80% of the MDA-MB468 cells could be killed by pIC/PPGE11 at 0.1 μg/ml with minimal effect on the control cells.

7.4 Efficacy of First- and Second-Generation Vectors In Vivo.

Figure 8A:
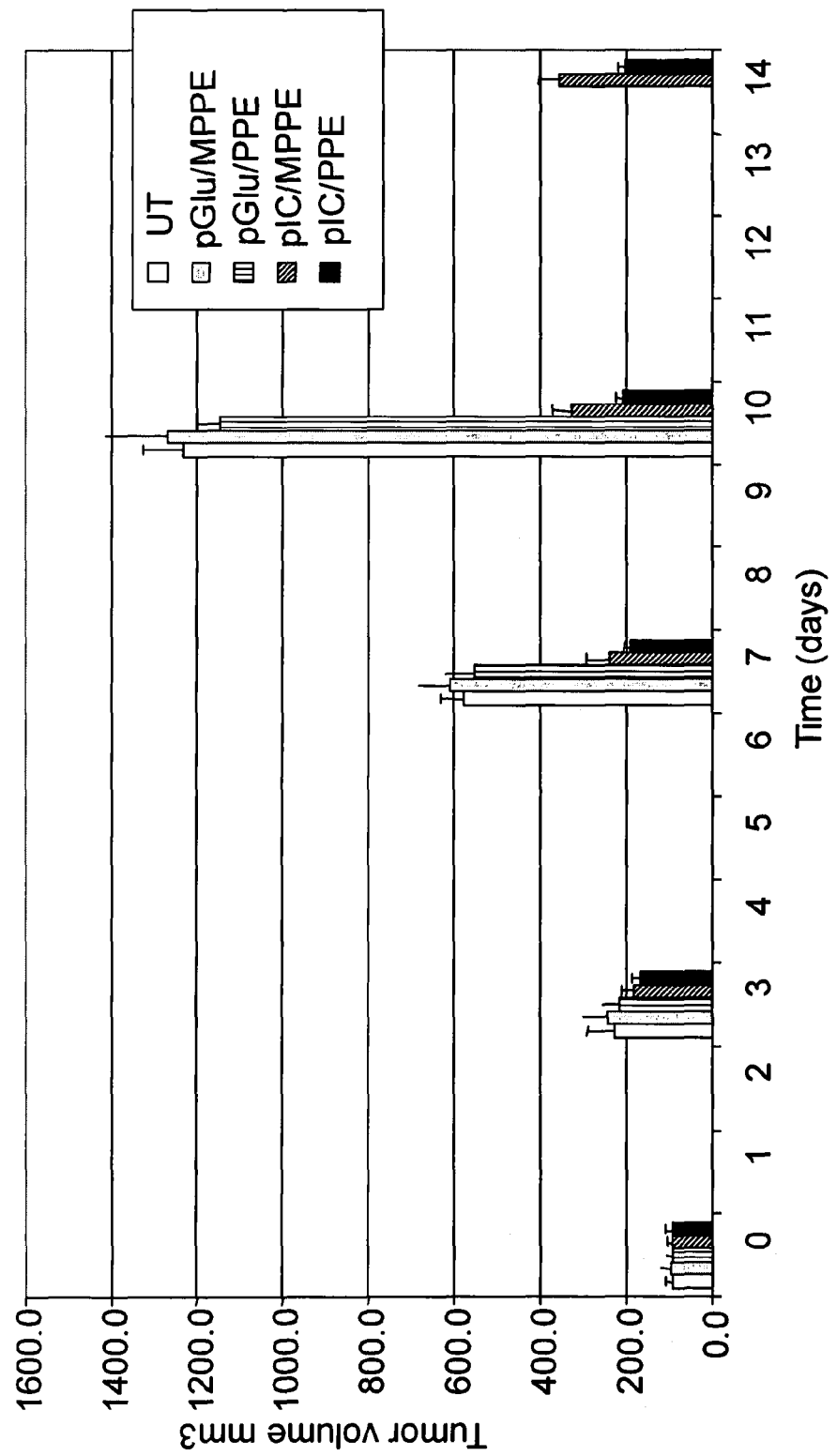
FIGS. 8A-B show the effect of different vectors (pGlu/MPPE, pGlu/PPE, pIC/MPPE and pIC/PPE) in vivo on s.c. A431 growth in nude mice. For the experiment depicted in 8A, female 4-5 week old mice were injected s.c. with 2 million A431 cells (human epithelial carcinoma cell line that express high levels of EGFR) dissolved in 200 µl PBS. When the tumors reached ~80 mm$^3$, mice were divided into 5 groups with 5 animals per group. 10 µg of pIC formulated with the indicated conjugate were injected IV every 48 hrs. For the experiment depicted in 8B, female 6-7 week old mice were injected s.c with 2 million U138MG cells dissolved in 100 μl PBS. When the tumors reached ~75 mm³, mice were divided into 3 groups with 9 animals per group. Mice were then injected IV with the indicated dose of pIC/P$_{221}$PE (10 or 25 μg/mouse once every 48 hours). pGlu, polyglutamic acid.
Figure 8B:
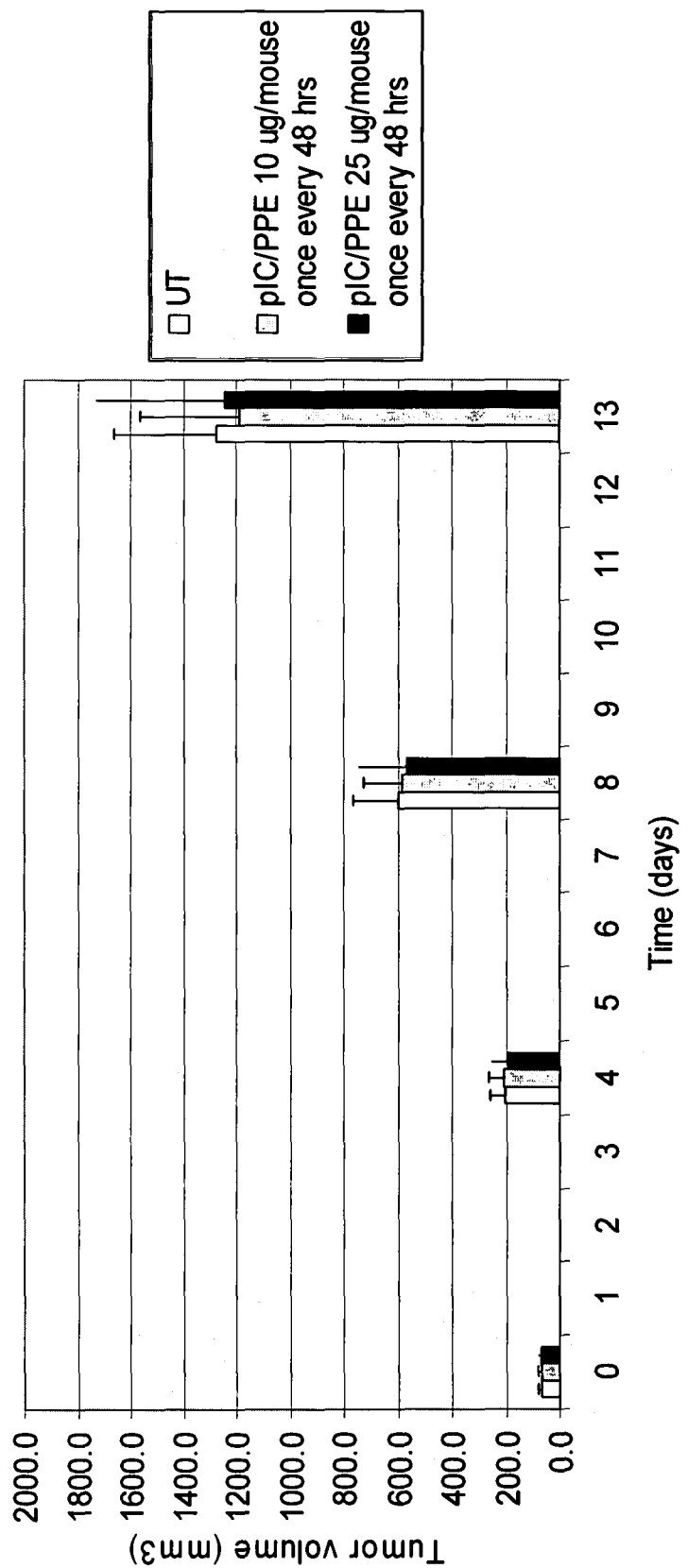

The efficacy of $pIC/P_{221}PE$ and pIC/MPPE was further compared in vivo. Female mice were injected s.c. with 2 million A431 cells dissolved in PBS. When the tumors reached the size of about 75-80 mm$^3$, mice were divided into 5 groups. pIC formulated with the indicated conjugate was injected IV every 48 hrs. pIC/PPE showed even stronger efficiency than pIC/MPPE in inhibition of A431 tumor growth (FIG. 8A), and pIC/PPE preserved its selectivity as can be seen from the lack of influence on the growth of U138MG tumors (which do not express EGFR) even at high doses (FIG. 8B).

REFERENCES

Butowski N, et al. (2009) A phase II clinical trial of poly-ICLC with radiation for adult patients with newly diagnosed supratentorial glioblastoma: a North American Brain Tumor Consortium (NABTC01-05). J Neurooncol 91:175-82.

Ciceri F, et al. (2007) Antitumor effects of HSV-TK-engineered donor lymphocytes after allogeneic stem-cell transplantation. Blood 109:4698-707.

Fujimura T, Nakagawa S, Ohtani T, Ito Y, Aiba S (2006) Inhibitory effect of the polyinosinic-polycytidylic acid/cationic liposome on the progression of murine B16F10 melanoma. Eur J Immunol 36:3371-80.

Hynes N E, MacDonald G (2009) ErbB receptors and signaling pathways in cancer. Curr Opin Cell Biol 21:177-84.

Li, Z. et al. (2005) Identification and characterization of a novel peptide ligand of epidermal growth factor receptor for targeted delivery of therapeutics, FASEB J. 19:1978-85.

Rosenberg S A (2008) Overcoming obstacles to the effective immunotherapy of human cancer. Proc Natl Acad Sci USA 105:12643-4.

Salazar A M, et al. (1996) Long-term treatment of malignant gliomas with intramuscularly administered polyinosinic-polycytidylic acid stabilized with polylysine and carboxymethylcellulose: an open pilot study. Neurosurgery 38:1096-103; discussion 1103-4.

Shir. A, Ogris M, Wagner E, Levitzki A (2006) EGF receptor-targeted synthetic double-stranded RNA eliminates glioblastoma, breast cancer, and adenocarcinoma tumors in mice. PLoS Med 3:e6.

Song, S. et al. (2008) Peptide ligand-mediated liposome distribution and targeting to EGFR expressing tumors in vivo, Int J Pharmaceuticals 363: 155-161.

The invention claimed is:

1. A pharmaceutical composition for systemic administration comprising a pharmaceutically acceptable carrier and an EGFR-homing vector selected from the group consisting of a vector comprising polyinosinic-polycytidylic acid double stranded RNA; unbranched polyethyleneimine covalently linked to polyethylene glycol; and mEGF (pIC/PPE) and a vector comprising polyinosinic-polycytidylic acid double stranded RNA; unbranched polyethyleneimine covalently linked to polyethylene glycol; and peptide GE11 (pIC/PPGE11).

2. An EGFR-homing vector selected from the group consisting of a vector comprising polyinosinic-polycytidylic acid double stranded RNA; unbranched polyethyleneimine covalently linked to polyethylene glycol; and mEGF (pIC/PPE) and a vector comprising polyinosinic-polycytidylic acid double stranded RNA; unbranched polyethyleneimine covalently linked to polyethylene glycol; and peptide GE11 (pIC/PPGE11).

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1
```

-continued

```
Tyr His Trp Tyr Gly Tyr Thr Pro Gln Asn Val Ile
1               5                   10
```